US010039552B2

(12) United States Patent
Kratzberg et al.

(10) Patent No.: US 10,039,552 B2
(45) Date of Patent: Aug. 7, 2018

(54) MAGNETICALLY ACTUATED GATING DEVICES, SYSTEMS, KITS, AND METHODS

(71) Applicants: Jarin Kratzberg, Lafayette, IN (US); Keith Milner, West Lafayette, IN (US); Sara Sherman, Lafayette, IN (US); Adam Shields, Lafayette, IN (US)

(72) Inventors: Jarin Kratzberg, Lafayette, IN (US); Keith Milner, West Lafayette, IN (US); Sara Sherman, Lafayette, IN (US); Adam Shields, Lafayette, IN (US)

(73) Assignees: COOK MEDICAL TECHNOLOGIES LLC, Bloomington, IN (US); COOK REGENTEC LLC, Indianapolis, IN (US)

( * ) Notice: Subject to any disclaimer, the term of this patent is extended or adjusted under 35 U.S.C. 154(b) by 309 days.

(21) Appl. No.: 14/924,188

(22) Filed: Oct. 27, 2015

(65) Prior Publication Data
US 2016/0113654 A1    Apr. 28, 2016

Related U.S. Application Data

(60) Provisional application No. 62/069,371, filed on Oct. 28, 2014.

(51) Int. Cl.
*A61B 17/122* (2006.01)
*A61B 17/00* (2006.01)
*A61B 17/132* (2006.01)

(52) U.S. Cl.
CPC .......... *A61B 17/122* (2013.01); *A61B 17/132* (2013.01); *A61B 2017/00411* (2013.01); *A61B 2017/00876* (2013.01)

(58) Field of Classification Search
CPC .............. A61B 17/12; A61B 17/12009; A61B 17/12013; A61B 17/122; A61B 17/128;
(Continued)

(56) References Cited

U.S. PATENT DOCUMENTS 2,921,584 A * 1/1960 Di Vette ................. A61B 17/12
251/9
3,419,008 A    12/1968 Plishner
(Continued)

FOREIGN PATENT DOCUMENTS

WO    WO2007016122 A2    2/2007

OTHER PUBLICATIONS

Medtronic Neurosurgery, "Pediatric Shunt Case using a Strata II Valve with William Louden MD," Youtube.com, published Jul. 5, 2013, accessed Sep. 11, 2014, http://www.youtube.com/watch?v=YR5JplX3LS4.
(Continued)

*Primary Examiner* — Ryan J Severson
(74) *Attorney, Agent, or Firm* — Buchanan Van Tuinen LLC

(57) ABSTRACT

Magnetically actuated gating devices, magnetically actuated gating systems, magnetically actuated gating kits, and methods of treatment using a magnetically actuated gating device are described herein. An example embodiment of a magnetically actuated gating device comprises a housing, a rotatable member, a compression member, and a membrane. The rotatable member has a first magnetic field that is configured to interact with a second magnetic field produced by an external element to move the rotatable member between a first position and a second position.

20 Claims, 7 Drawing Sheets

(58) Field of Classification Search
CPC .............. A61B 17/1285; A61B 17/132; A61B 17/1322; A61B 17/1325; A61B 2017/00411; A61B 2017/00778; A61B 2017/00876; A61B 2017/12004
See application file for complete search history.

(56) References Cited

U.S. PATENT DOCUMENTS

| | | | |
|---|---|---|---|
| 3,675,656 A | | 7/1972 | Hakim |
| 3,699,957 A | | 10/1972 | Robinson |
| 3,730,186 A | | 5/1973 | Edmunds, Jr. et al. |
| 3,744,063 A | | 7/1973 | McWhorter et al. |
| 3,749,098 A | * | 7/1973 | De Bennetot ......... A61F 2/0036 251/65 |
| 3,750,194 A | | 8/1973 | Summers |
| 3,817,237 A | | 6/1974 | Bolduc |
| 3,926,175 A | | 12/1975 | Allen et al. |
| 3,939,821 A | | 2/1976 | Roth |
| 4,014,318 A | * | 3/1977 | Dockum ............. A61M 1/1053 137/527 |
| 4,024,855 A | * | 5/1977 | Bucalo ................. A61F 2/0036 128/843 |
| 4,080,958 A | | 3/1978 | Bregman et al. |
| 4,245,358 A | | 1/1981 | Moasser |
| 4,256,093 A | | 3/1981 | Helms et al. |
| 4,408,597 A | | 10/1983 | Tenney, Jr. |
| 4,417,360 A | | 11/1983 | Moasser |
| 4,551,862 A | | 11/1985 | Haber |
| 4,552,128 A | | 11/1985 | Haber |
| 4,828,544 A | | 5/1989 | Lane et al. |
| 4,958,630 A | | 9/1990 | Rosenbluth et al. |
| 4,982,731 A | | 1/1991 | Lue et al. |
| 5,366,506 A | | 11/1994 | Davis |
| 5,453,079 A | | 9/1995 | Schwaninger |
| 5,762,599 A | | 6/1998 | Sohn |
| 5,797,879 A | | 8/1998 | DeCampli |
| 6,053,891 A | * | 4/2000 | DeCampli ............. A61B 5/6862 604/288.01 |
| 6,162,238 A | | 12/2000 | Kaplan et al. |
| 6,409,656 B1 | | 6/2002 | Sangouard et al. |
| 6,547,801 B1 | | 4/2003 | Dargent et al. |
| 6,616,624 B1 | | 9/2003 | Kieval |
| 7,011,621 B2 | * | 3/2006 | Sayet ..................... A61F 2/0036 600/30 |
| 7,128,750 B1 | * | 10/2006 | Stergiopulos .......... A61B 17/12 606/157 |
| 7,367,938 B2 | | 5/2008 | Forsell |
| 7,479,105 B2 | | 1/2009 | Matsumura |
| 7,485,104 B2 | * | 2/2009 | Kieval ................. A61M 1/367 600/16 |
| 7,762,980 B2 | | 7/2010 | Gertner |
| 8,079,974 B2 | * | 12/2011 | Stergiopulos .......... A61B 17/12 604/9 |
| 8,096,989 B2 | | 1/2012 | Buffard et al. |
| 8,114,044 B2 | | 2/2012 | Cull |
| 8,152,711 B2 | | 4/2012 | Gross |
| 8,226,592 B2 | | 7/2012 | Brenneman et al. |
| 8,382,652 B2 | * | 2/2013 | Sayet ..................... A61F 2/0036 600/30 |
| 8,506,517 B2 | | 8/2013 | Stergiopulos |
| 8,728,105 B2 | | 5/2014 | Aguirre |
| 8,932,247 B2 | * | 1/2015 | Stergiopulos .......... A61B 17/12 604/9 |
| 9,144,482 B2 | * | 9/2015 | Sayet ..................... A61F 2/0036 |
| 9,226,753 B2 | | 1/2016 | Surti et al. |
| 2004/0015159 A1 | | 1/2004 | Slater et al. |
| 2007/0027460 A1 | | 2/2007 | Case et al. |
| 2016/0113654 A1 | * | 4/2016 | Kratzberg ............ A61B 17/122 606/158 |

OTHER PUBLICATIONS

Medtronic, "Strata Valves," Medtronic.com, last updated Oct. 8, 2002, accessed Sep. 11, 2014, http://medtronic.com/patients/hydrocephalus/device/our-shunts/strata-valves/index.htm.

* cited by examiner

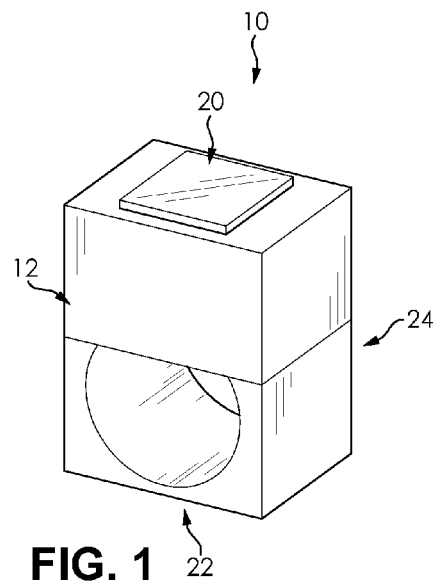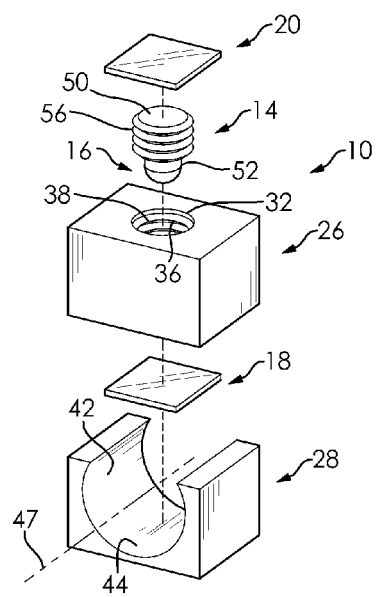
FIG. 1
FIG. 2
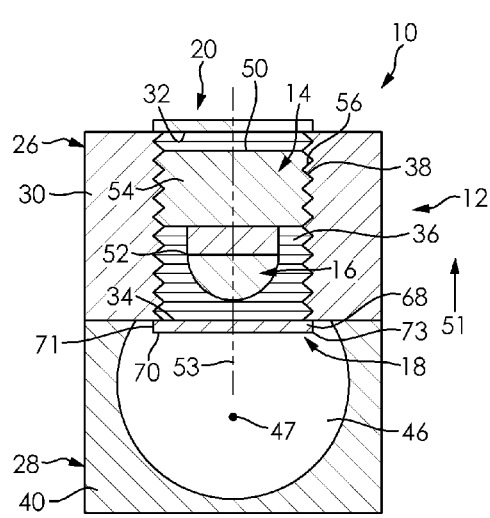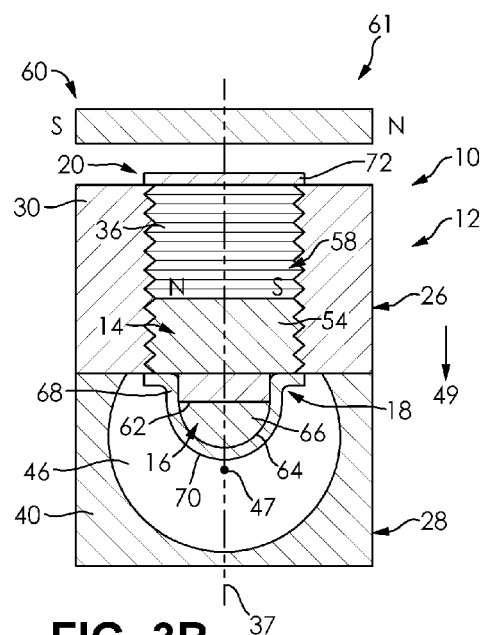
FIG. 3A
FIG. 3B

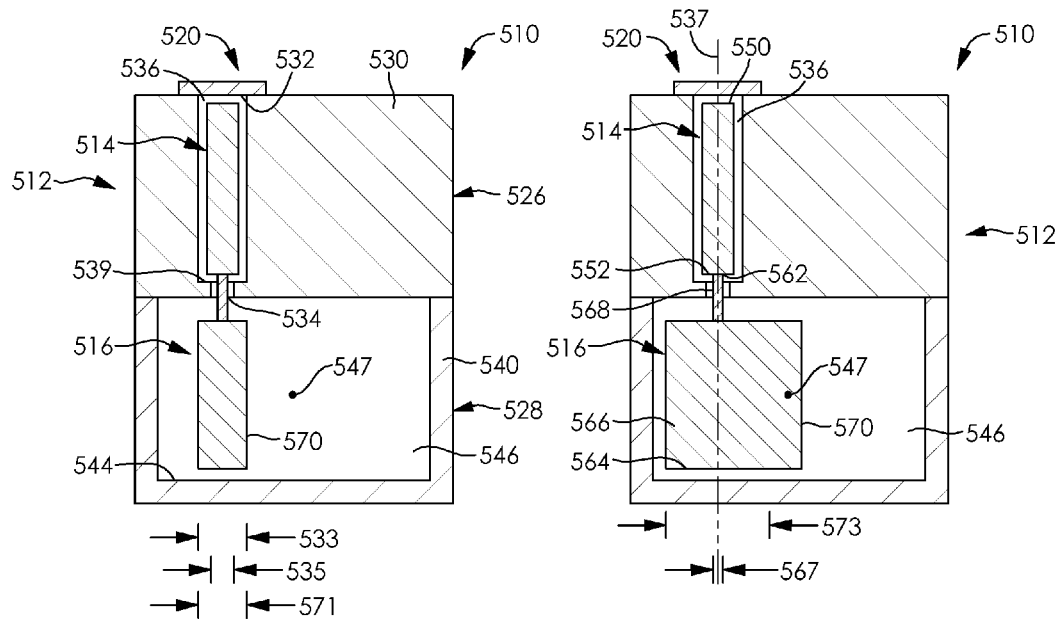
FIG. 11A  FIG. 11B
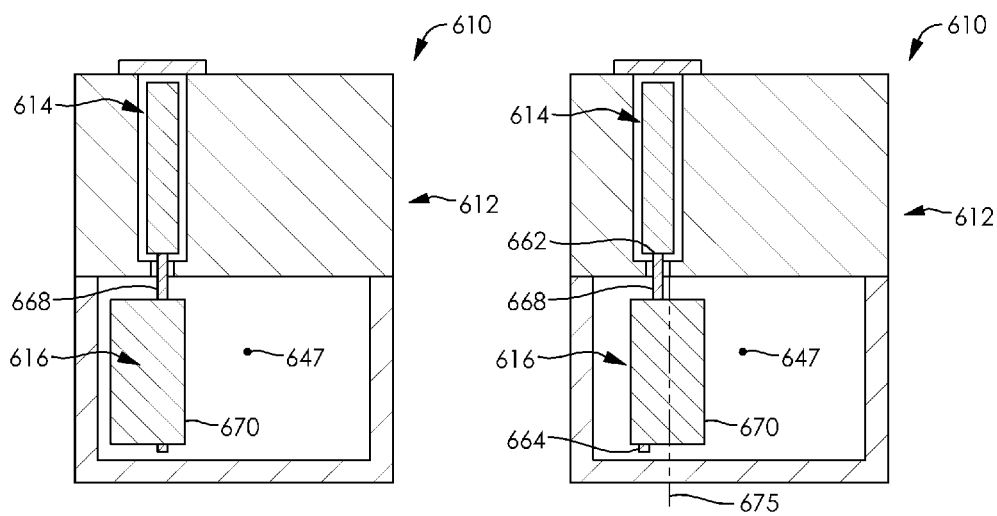
FIG. 12A  FIG. 12B

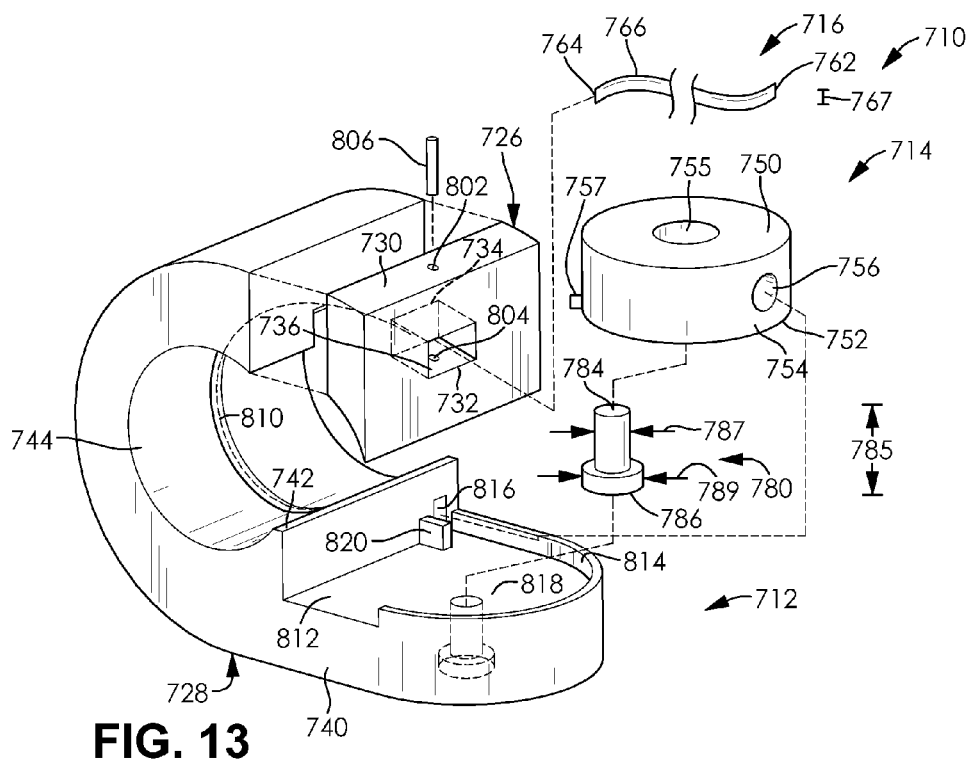
FIG. 13
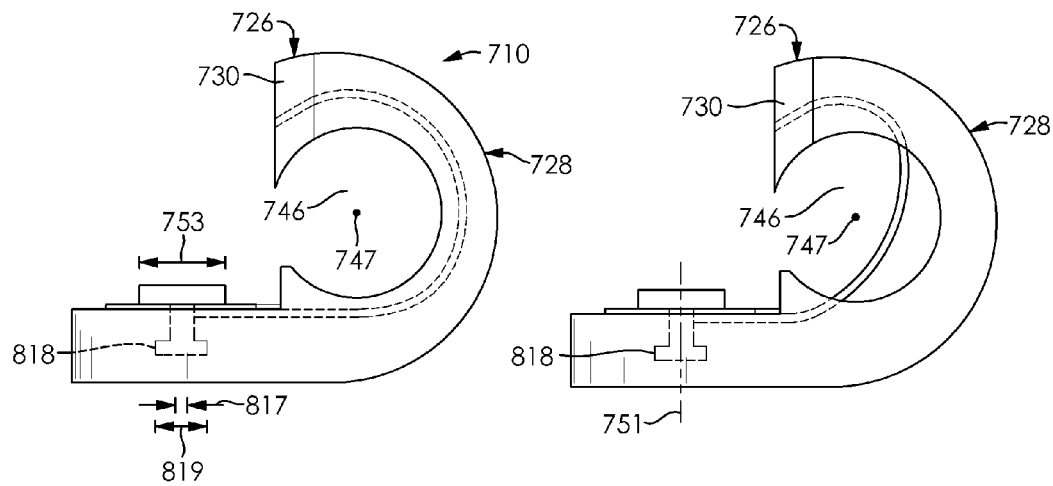
FIG. 14A     FIG. 14B

MAGNETICALLY ACTUATED GATING DEVICES, SYSTEMS, KITS, AND METHODS

RELATED APPLICATION

This application claims the benefit of U.S. Provisional Application No. 62/069,371, filed Oct. 28, 2014. The entire disclosure of this related application is hereby incorporated into this disclosure by reference.

FIELD

The disclosure relates generally to the field of medical devices and methods of treatment. More particularly, the disclosure relates to the field of vessel gating devices, vessel gating systems, vessel gating kits, and methods of treatment that use vessel gating devices.

BACKGROUND

End-stage renal disease (ESRD) is a condition characterized by the permanent failure of the kidneys to function well enough to meet the needs of daily life. Treatment of ESRD varies depending on the degree of kidney function that remains and generally requires a kidney transplant or dialysis. However, due to the lack of kidneys available for transplantation, most patients are treated by dialysis.

Hemodialysis, a frequently used form of dialysis, transfers blood from the body through an artificial kidney, or dialyzer, such that waste can be removed from the blood before it is returned to the body. To minimize treatment time, hemodialysis requires a large blood volume flow rate, which is typically achieved through the surgical creation of an arteriovenous fistula (AVF). While an increased blood flow may be desired during hemodialysis, an unregulated blood flow may create complications, such as preventing proper fistula maturation. Therefore, the ability to control the patency of an AVF such that blood flow can be regulated prior to, during, or subsequent to treatment may benefit patients by reducing the complications associated with AVFs and assist with fistula maturation.

A variety of medical devices have been developed that provide a mechanism for controlling the patency of a vessel within a body. However, existing devices are difficult to manipulate between various configurations such that the patency of the vessel can be modified prior to, during, or subsequent to treatment. Therefore, a need exists for improved medical devices, systems, kits, and methods that provide a mechanism for controlling the patency of a vessel.

BRIEF SUMMARY OF SELECTED EXAMPLE EMBODIMENTS

Magnetically actuated gating devices useful in manipulating the patency of a vessel are provided, including magnetically actuated gating devices useful in manipulating the patency of an arteriovenous fistula. An example embodiment of a magnetically actuated gating device comprises a housing, a rotatable member, and a compression member. The magnetically actuated gating device is suitable for implantation outside of a vessel and is adapted to interact with an element located exterior to the vessel. The element has a first magnetic field and is moveable in a first direction and a second direction that is substantially opposite the first direction. The housing defines a first passageway, a second passageway, and a first opening. The first passageway has a first lengthwise axis. The second passageway is configured to receive a portion of the vessel and has a second lengthwise axis that is disposed at an angle to the first lengthwise axis. The first opening provides access between the first passageway and the second passageway. The rotatable member is rotatably attached to the housing and is moveable between a first position and a second position. The rotatable member is disposed within the first passageway and has a second magnetic field that is adapted to interact with the first magnetic field such that the rotatable member moves from its first position to its second position when the element is moved in the first direction and moves from its second position to its first position when the element is moved in the second direction. The compression member is attached to the rotatable member and is adapted to move between a first position in which the compression member is disposed a first distance from the second lengthwise axis and a second position in which the compression member is disposed a second distance from the second lengthwise axis. The second distance is different than the first distance. The compression member is in the first position when the rotatable member is in the first position and is in the second position when the rotatable member is in the second position.

Another example embodiment of a magnetically actuated gating device comprises a housing, a rotatable member, a compression member, and a membrane. The magnetically actuated gating device is suitable for implantation outside of a vessel and is adapted to interact with an element located exterior to the vessel. The element has a first magnetic field and is moveable in a first direction and a second direction that is substantially opposite the first direction. The housing defines a first passageway, a second passageway, and a first opening. The first passageway has a first lengthwise axis. The second passageway is configured to receive a portion of the vessel and has a second lengthwise axis that is disposed at an angle to the first lengthwise axis. The first opening provides access between the first passageway and the second passageway. The rotatable member is rotatably attached to the housing and is moveable between a first position and a second position. The rotatable member is disposed within the first passageway, has a magnetically actuated member, and defines a recess. The magnetically actuated member is attached within the recess and has a second magnetic field that is adapted to interact with the first magnetic field such that the rotatable member moves from its first position to its second position when the element is moved in the first direction and moves from its second position to its first position when the element is moved in the second direction. The compression member is attached to the rotatable member and is adapted to move between a first position in which the compression member is disposed a first distance from the second lengthwise axis and a second position in which the compression member is disposed a second distance from the second lengthwise axis. The second distance is different than the first distance. The compression member is in the first position when the rotatable member is in the first position and is in the second position when the rotatable member is in the second position. The membrane is attached to the housing and disposed over the first opening. The membrane prevents fluid within the second passageway from passing into the first passageway and is adapted to move between a first position in which the membrane is disposed a first distance from the second lengthwise axis and a second position in which the membrane is disposed a second distance from the second lengthwise axis that is different than the first distance. The membrane is in the first position when the rotatable member is in the first position and is in the second position when the rotatable member is in the second position.

Another example embodiment of a magnetically actuated gating device comprises a housing, a rotatable member, a compression member, and a membrane. The magnetically actuated gating device is suitable for implantation outside of a vessel and is adapted to interact with an element located exterior to the vessel. The element has a first magnetic field and is moveable in a first direction and a second direction that is substantially opposite the first direction. The housing defines a first passageway, a second passageway, and a first opening. The housing is formed of a first material. The first passageway has a first lengthwise axis. The second passageway is configured to receive a portion of the vessel and has a second lengthwise axis that is disposed orthogonal to the first lengthwise axis. The first opening provides access between the first passageway and the second passageway. The rotatable member is rotatably attached to the housing and is moveable between a first position and a second position. The rotatable member is disposed within the first passageway, has a magnetically actuated member, and defines a recess. The magnetically actuated member is attached within the recess and has a second magnetic field that is adapted to interact with the first magnetic field such that the rotatable member moves from its first position to its second position when the element is moved in the first direction and moves from its second position to its first position when the element is moved in the second direction. The compression member is attached to the rotatable member and is adapted to move between a first position in which the compression member is disposed a first distance from the second lengthwise axis and a second position in which the compression member is disposed a second distance from the second lengthwise axis. The second distance is different than the first distance. The compression member is in the first position when the rotatable member is in the first position and is in the second position when the rotatable member is in the second position. The membrane is attached to the housing and disposed over the first opening between the compression member and the second passageway. The membrane prevents fluid within the second passageway from passing into the first passageway and is adapted to move between a first position in which the membrane is disposed a first distance from the second lengthwise axis and a second position in which the membrane is disposed a second distance from the second lengthwise axis that is different than the first distance. The membrane is in the first position when the rotatable member is in the first position and is in the second position when the rotatable member is in the second position. The membrane is formed of a second material that is different than the first material.

Kits useful in the performance of methods of treatment are also provided. An example kit comprises a magnetically actuated gating device according to an embodiment and an element that has a magnetic field.

Methods of treatment using a magnetically actuated gating device are also provided. An example method of treatment comprises creating an opening in a portion of a body that provides access to a vessel; positioning a magnetically actuated gating device on the vessel; closing the opening that provides access to the vessel; applying an external second magnetic field to the first magnetic field of the magnetically actuated gating device such that the rotatable member moves from the first position to the second position; allowing an interval of time to pass; applying an external second magnetic field to the first magnetic field of the magnetically actuated gating device such that the rotatable member moves from the second position to the first position.

Additional understanding of the exemplary magnetically actuated gating devices, systems, kits, and methods can be obtained by review of the detailed description, below, and the appended drawings.

BRIEF DESCRIPTION OF THE DRAWINGS

FIG. 1 is a perspective view of an example embodiment of a gating device in a first configuration.

FIG. 2 is an exploded perspective view of the gating device illustrated in FIG. 1.

FIG. 3A is a sectional view of the gating device illustrated in FIG. 1 taken along the lengthwise axis of the housing. The gating device is in a first configuration.

FIG. 3B is a sectional view of the gating device illustrated in FIG. 1 taken along the lengthwise axis of the housing. The gating device is in a second configuration. An exterior element having a magnetic field is also illustrated.

FIG. 11A is a sectional view of another example embodiment of a gating device taken along the lengthwise axis of the housing. The gating device is in a first configuration.

FIG. 11B illustrates the gating device shown in FIG. 11A in a second configuration.

FIG. 12A is a sectional view of another example embodiment of a gating device taken along the lengthwise axis of the housing. The gating device is in a first configuration.

FIG. 12B illustrates the gating device shown in FIG. 12A in a second configuration.

FIG. 13 is an exploded view of another example embodiment of a gating device.

FIG. 14A is an elevation view of the gating device illustrated in FIG. 13. The gating device is assembled and in a first configuration.

FIG. 14B is an elevation view of the gating device illustrated in FIG. 13. The gating device is assembled and in a second configuration.

DETAILED DESCRIPTION

Figure 4:
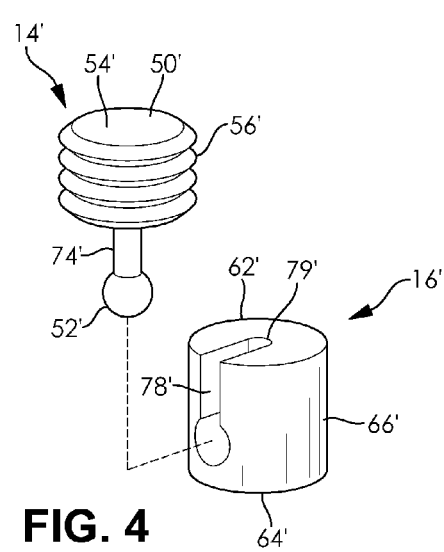
FIG. 4 is an exploded perspective view of an example alternative rotatable member and compression member.

The following detailed description and the appended drawings describe and illustrate various example embodiments of magnetically actuated gating devices, magnetically actuated gating systems, magnetically actuated gating kits, and methods of treatment using a magnetically actuated gating device. The description and illustration of these examples are provided to enable one skilled in the art to make and use a magnetically actuated gating device, a magnetically actuated gating system, magnetically actuated gating kit, and to practice a method of treatment using a magnetically actuated gating device. They are not intended to limit the scope of the claims in any manner.

The use of "e.g.," and "or," and grammatically related terms, indicate non-exclusive alternatives without limitation, unless otherwise noted. The use of "attached," and grammatically related terms, refers to the fixed, releasable, or integrated association of two or more elements and/or devices, unless otherwise noted. The use of "diameter" refers to the length of a straight line passing from side to side through the center of a body, element, or feature, and does not impart any structural configuration on the body, element, or feature. The use of "circumference" refers to the distance around the exterior surface of a body, element, or feature, and does not impart any structural configuration on the body, element, or feature. The term "vessel," and grammatically related terms, refers to tubular members, any structures that transport material, such as structures that transport material in the body of an animal, walls that define bodily passages, arteries, veins, fistulas, arteriovenous fistulas, capillaries, portions of the urinary tract, lymphatic vessels, vessels in the digestive tract, natural body vessels, prosthetic body vessels, and grafts, such as autologous grafts, homologous grafts, or synthetic grafts.

FIGS. 1, 2, 3A, and 3B illustrate an example embodiment of a magnetically actuated gating device 10 that includes a housing 12, a rotatable member 14, a compression member 16, a membrane 18, and a cap 20. The magnetically actuated gating device 10 is moveable between a first configuration, as shown in FIG. 3A, and a second configuration, as shown in FIG. 3B.

The housing 12 has a first end 22, a second end 24, a top member 26, and a bottom member 28. The top member 26 has a body 30 that defines a first opening 32, a second opening 34, a first passageway 36, and threads 38. The first passageway 36 extends from the first opening 32 to the second opening 34 and has a first lengthwise axis 37, as shown in FIG. 3B. The threads 38 extend from the first opening 32 to the second opening 34 and are sized and configured to interact with the threads 56 defined by the rotatable member 14, as described herein. However, alternative embodiments can include a top member that defines threads that extend between the first opening and the second opening, from the first opening toward the second opening, from the second opening toward the first opening, and any other configuration considered suitable for a particular embodiment.

As shown in FIG. 2, the bottom member 28 has a body 40 that defines a slit 42 and a recess 44. The slit 42 is defined on a surface that is directed toward the top member 26 when the top member 26 and bottom member 28 are attached to one another. The slit 42 extends from the first end 22 to the second end 24 of the housing 12 such that it interrupts the surface that is directed toward the top member 26 when the housing 12 is assembled, as shown in FIG. 1. The recess 44 extends from the slit 42, into the body 40 of the bottom member 28, and from the first end 22 to the second end 24 of the housing 12. The recess 42 is sized and configured to receive a vessel. In the illustrated embodiment, the recess 44 has a semi-circular cross-sectional structural configuration. However, a recess defined by a housing can have any suitable cross-sectional structural configuration, such as a recess that is semioval, crescent-shaped, rectangular, square, and any other cross-sectional configuration considered suitable for a particular embodiment.

When assembled, as shown in FIGS. 1, 3A, and 3B, the top member 26 and the bottom member 28 are releasably attached to one another such that the recess 42 and a portion of the body 30 of the top member 26 cooperatively define a second passageway 46 that is sized and configured to receive a vessel. The second passageway 46 has a second lengthwise axis 47. Thus, the housing 12 defines a first passageway 36 and a second passageway 46. When assembled, the slit 42 of the bottom member 28 is aligned with the first passageway 36 such that the rotatable member 14 can be advanced into the second passageway 46, as described in more detail herein. In the illustrated embodiment, the first lengthwise axis 37 of the first passageway 36 is disposed orthogonally to the second lengthwise axis 47 of the second passageway 46. However, alternative embodiments can include a first passageway that has a first lengthwise axis that is disposed at other angles relative to a second lengthwise axis of a second passageway. For example, a first lengthwise axis can be disposed parallel to a second lengthwise axis, offset from a second lengthwise axis such that the first lengthwise axis does not intersect the second lengthwise axis, at an angle to a second lengthwise axis (e.g., 45 degree angle, acute angles, obtuse angles), on a first plane that is disposed orthogonal to a second plane on which a second lengthwise axis is disposed, on a first plane that is disposed at an angle to a second plane on which a second lengthwise axis is disposed, or any other structural arrangement considered suitable for a particular embodiment.

The top member 26 and the bottom member 28 can be releasably attached to one another using any suitable technique and/or method of attachment. Skilled artisans will be able to select a suitable technique and/or method of attachment between a top member and a bottom member according to a particular embodiment based on various considerations, including the material(s) that forms the top member and/or bottom member. For example, the top member and the bottom member can include mating snap fit structures, morse taper configurations, one or more magnetics, and/or any other structure capable of providing releasable attachment between the top member and the bottom member. Alternatively, or in combination with the examples described above, a top member can define one or more threaded passageways that are each in communication with a threaded passageway defined by a bottom member such that a screw (e.g., machine screw) can be partially disposed within each passageway of the top member and each passageway of the bottom member to releasably attach the top member to the bottom member.

While the housing 12 has been illustrated as having a particular structural configuration, a housing included in a magnetically actuated gating device can have any suitable structural configuration. Skilled artisans will be able to select a suitable configuration for a housing that is intended to be included in a magnetically actuated gating device according to a particular embodiment based on various considerations, including the treatment intended to be performed. For example, a housing can be cylindrical, cuboidal, a cube, a triangular prism, a sphere, a semi-sphere, and any other configuration considered suitable for a particular embodiment. While housing 12 has been illustrated as defining a first passageway 36 and a second passageway 46, a housing can define any suitable number of passageways. Example number of passageways considered suitable for a housing to define include one, at least one, two, a plurality, three, four, and any other number considered suitable for a particular embodiment.

The housing 12 can have any suitable dimensions, and skilled artisans will be able to select suitable dimensions for a housing according to a particular embodiment based on various considerations, including the dimensions of a vessel on which the magnetically actuated gating device is intended to be used. Example dimensions considered suitable for a housing include those that provide a structure that is sized and configured to be implanted within the body of a patient (e.g., within the forearm of a patient, within the lower half of a patient's forearm, within the upper half of the patient's forearm). Additional example dimensions considered suitable for a housing include those that are capable of defining a first passageway that is sized and configured to receive a rotatable member and/or compression member and/or those capable of defining a second passageway that is sized and configured to receive a membrane and/or a vessel.

The housing 12 can be formed of any suitable material and can be fabricated using any suitable method or technique. Skilled artisans will be able to select a suitable material to form a housing and a suitable method or technique to fabricate a housing according to a particular embodiment based on various considerations, including the material(s) that forms a rotatable member included in a magnetically actuated gating device of which the housing is a component. Example materials considered suitable to form a housing include biocompatible materials, materials that can be made biocompatible, non-ferromagnetic materials, materials that are magnetic-resonance compatible, materials that are magnetic-resonance safe, metals such as stainless steel, titanium, nickel-titanium alloys (e.g., Nitinol), polymers, Pebax (Pebax is a registered trademark of AtoChimie Corporation of Allee des Vosges, Courbevoie, France), nylon, polyethylene, polyurethane, silicone, combinations of the materials described herein, and any other material considered suitable for a particular application. Example methods and techniques considered suitable to fabricate a housing include extrusion processes, molding processes, injection molding processes, casting processes, and any other method or technique considered suitable for a particular embodiment.

The rotatable member 14 has a first end 50, a second end 52, a lengthwise axis 53, and a body 54 that defines threads 56. The threads 56 extend outward from the body 54 and away from the lengthwise axis 53 of the rotatable member 14 and from the first end 50 toward the second end 52. The threads 56 are sized and configured to interact with the threads 38 defined by the top member 26. However, alternative embodiments can include a rotatable member that defines threads that extend between the first end and the second end, from the second end toward the first end, and any other configuration considered suitable for a particular embodiment.

The rotatable member 14 is moveable between a first position, as shown in FIG. 3A, and a second position, as shown in FIG. 3B. The first end 50 of the rotatable member 14 is disposed a first distance from the second lengthwise axis 47 when the rotatable member 14 is in the first position. The first end 50 of the rotatable member 14 is disposed a second distance from the second lengthwise axis 47 when the rotatable member 14 is in the second position. The first distance is greater than the second distance. In the illustrated embodiment, the rotatable member 14 has a first magnetic field 58, as shown in FIG. 3B, that is adapted to interact with a second magnetic field 60 produced by an element 61 positioned exterior to the housing 12. Rotation of the second magnetic field 60 rotates the rotatable member 14, which results in axial translation of the rotatable member 14 within the first passageway 36 along the first lengthwise axis 37. Thus, the application of a rotating external second magnetic field 60 to the first magnetic field 58 results in movement of the rotatable member 14 between its first and second positions.

The rotatable member 14 can be formed of any suitable material and can be fabricated using any suitable method or technique. Skilled artisans will be able to select a suitable material to form a rotatable member and a suitable method or technique to fabricate a rotatable member according to a particular embodiment based on various considerations, including the material(s) that forms a housing included in a magnetically actuated gating device of which the rotatable member is a component. Example materials considered suitable to form a rotatable member include biocompatible materials, materials that can be made biocompatible, materials that produce a magnetic field, materials that can be made magnetic, materials that can be magnetized, materials that form permanent magnets, ferromagnetic materials, ferrite, permanent magnets, rare-earth permanent magnets, metals such as stainless steel, titanium, nickel-titanium alloys (e.g., Nitinol), polymers, Pebax, nylon, polyethylene, polyurethane, silicone, combinations of the materials described herein, and any other material considered suitable for a particular application. Example methods and techniques considered suitable to fabricate a rotatable member include extrusion processes, molding processes, injection molding processes, casting processes, and any other method or technique considered suitable for a particular embodiment. For example, a rotatable member included in a magnetically actuated gating device can be formed of a material that has been magnetized across its diameter, along an axis that is orthogonal to the lengthwise axis of the rotatable member, such that the rotatable member is a diametrically magnetized element. In embodiments in which the rotatable member is diametrically magnetized, the rotatable member has a first magnetic pole on a first side and a second magnetic pole on a second side that is opposably facing the first side. The first magnetic pole is different than the second magnetic pole. Alternatively, a rotatable member can be magnetized such that it forms a series of magnetic north and south poles that alternate around the lengthwise axis and/or the circumference of the rotatable member.

The compression member 16 has a first end 62, a second curved end 64, and a body 66. The first end 62 of the compression member 16 is attached to the second end 52 of the rotatable member 14 and the second curved end 64 is directed toward the second passageway 46 defined by the housing 12. The second curved end 64 acts as an atraumatic tip that is configured to prevent damage to a vessel during use. In the illustrated embodiment, the compression member 16 is a separate element attached to the rotatable member 14 and is formed of a material that is different than the material that forms the rotatable member 14. Thus, the rotatable member 14 is formed of a first material and the compression member 16 is formed of a second material that is different than the first material. Alternatively, a rotatable member and a compression member can be formed of the same material and/or the compression member can be integrally formed with the rotatable member.

The compression member 16 can be attached to the rotatable member 14 using any suitable technique and/or method of attachment. Skilled artisans will be able to select a suitable technique and/or method of attachment between a rotatable member and compression member according to a particular embodiment based on various considerations, including the material(s) that forms the rotatable member and/or the compression member. For example, a rotatable member and a compression member can include mating snap fit structures, morse taper configurations, can be adhesively attached to one another, rotatably attached to one another, magnetically attached to one another, and/or any other technique or method of attachment considered suitable for a particular embodiment can be used to achieve attachment between the rotatable member and the compression member. The second passageway defined by a housing, a rotatable member, and/or a compression member included in a magnetically actuated gating device can be sized and configured such that when the rotatable member is in the second position the compression member is positioned near, or adjacent to, the surface that defines the second passageway.

The membrane 18 is attached to the housing 12 and has a body 68 that defines a first end 71, a second end 73, and a contact surface 70. The membrane 18 can be attached to the housing 12 using any suitable technique or method of attachment capable of providing a sealing engagement between the membrane 18 and the housing 12, such as using adhesive, friction fit structural attachments, or any other suitable technique or method of attachment, such as those described herein. In the illustrated embodiment, the first end 71 and the second end 73 of the membrane 18 are attached to the top member 26 such that the membrane 18 separates the first passageway 36 from the second passageway 46 (e.g., seals the first passageway 36) and prevents material from moving from the second passageway 46 into the first passageway 36. Thus, the first passageway 36 and the second passageway 46 are not in fluid communication with one another. Alternatively, a membrane can be attached to the bottom member of a housing, or a combination of the top member and the bottom member, such that the first passageway and the second passageway are separated from one another (e.g., not in fluid communication) when the housing is assembled.

The membrane 18 extends over the entire second opening 34 and comprises a flexible, or elastic, member that is moveable between a first position and a second position. In the first position, as shown in FIG. 3A, the membrane 18 is disposed a first distance from the second lengthwise axis 47 of the second passageway 46 and in the second position, as shown in FIG. 3B, the membrane 18 is disposed a second distance from the second lengthwise axis 47 that is different than the first distance. In the illustrated embodiment, the second distance is less than the first distance. The membrane 18 is in the first position when the rotatable member 14 is in the first position and is in the second position when the rotatable member 14 is in the second position.

In the illustrated embodiment, the housing 12 is formed of a first material and the membrane 18 is formed of a second material that is different than the first material. The second material is relatively more flexible, or elastic, than the first material. Alternatively, a housing and a membrane can be formed of the same material(s). The membrane 18 can be formed of any suitable material and can be fabricated using any suitable method or technique. Skilled artisans will be able to select a suitable material to form a membrane and a suitable method or technique to fabricate a membrane according to a particular embodiment based on various considerations, including the desired amount of flexibility and/or elasticity of the membrane. Example materials considered suitable to form a membrane include biocompatible materials, materials that can be made biocompatible, elastic materials, flexible materials, compliant materials, elastomeric materials, non-ferromagnetic materials, materials that are magnetic-resonance compatible, materials that are magnetic-resonance safe, polymers, Pebax, nylon, polyethylene, polyurethane, polyisoprene, polyethylene, polyvinyl chloride, polystyrene, silicone, silicone blends, combinations of the materials described herein, and any other material considered suitable for a particular application. For example, a membrane included in a magnetically actuated gating device can be formed of a portion of a non-compliant or compliant balloon, such as those used in dilation procedures. Example methods and techniques considered suitable to fabricate a membrane include casting processes, extrusion processes, molding processes, injection molding processes, and any other method or technique considered suitable for a particular embodiment. While the magnetically actuated gating device 10 has been illustrated as including a membrane 18, a magnetically actuated gating device can omit the inclusion of a membrane and the compression member can directly contact the vessel to move the vessel between a first configuration and a second configuration.

The cap 20 has a body 72 and is sized and configured to extend over the first opening 32 defined by the body 30 of the top member 26 such that fluid from an environment exterior to the first passageway 36 is prevented from entering the first passageway 36 through the first opening 32. Thus, the cap 20 seals the first opening 32 defined by the top member 28. The cap 20 can be attached to the top member 26 using any suitable technique or method of attachment capable of providing a sealing engagement between the cap 20 and the housing 12, such as using adhesive, friction fit structural attachments, or any other suitable technique or method of attachment, such as those described herein.

While the cap 20 has been illustrated as extending over the first opening 32, alternative embodiments can include a cap that is entirely, or partially disposed within, a first passageway defined by a housing and attached to the housing such that a sealing engagement between the cap and the housing is achieved. Alternatively, a magnetically actuated gating device can omit the inclusion of a cap and/or define a blind passageway that extends from an opening directed toward the bottom member and into the body of the top member.

In the illustrated embodiment, the cap 20 is formed of a first material and the housing 12 is formed of a second material that is the same as the first material. Alternatively, a housing and a cap can be formed of different materials. The cap 20 can be formed of any suitable material and can be fabricated using any suitable method or technique. Skilled artisans will be able to select a suitable material to form a cap and a suitable method or technique to fabricate a cap according to a particular embodiment based on various considerations, including the material(s) that forms a housing. Example materials considered suitable to form a cap include biocompatible materials, materials that can be made biocompatible, non-ferromagnetic materials, materials that are magnetic-resonance compatible, materials that are magnetic-resonance safe, metals such as stainless steel, titanium, nickel-titanium alloy (e.g., Nitinol), polymers, Pebax, nylon, polyethylene, polyurethane, silicone, combinations of the materials described herein, and any other material considered suitable for a particular application. Example methods and techniques considered suitable to fabricate a cap include extrusion processes, molding processes, injection molding processes, casting processes, and any other method or technique considered suitable for a particular embodiment.

The element 61 exterior to the housing 12 can be any suitable element, component, or device capable of producing, or that produces, a second magnetic field (e.g., alternating magnetic field, rotating magnetic field) that is adapted to interact with a first magnetic field to accomplish movement of a rotatable member between a first position and a second position, as described herein. In the illustrated embodiment, the element 61 exterior to the housing 12 is a bar magnet that can be rotated about the first lengthwise axis 37 of the first passageway 36 to produce rotation in the rotatable member 14. While a bar magnet has been illustrated, an element disposed external to a housing can be any suitable element, device, and/or system, that has a magnetic field, or is capable of producing or creating a magnetic field, such as a magnet, a permanent magnet, an electromagnet, a rotating electromagnet, and any other element, device, and/or system considered suitable for a particular embodiment. For example, an element exterior to the housing can comprise a diametrically magnetized element, a diametrically magnetized cylindrically shaped permanent magnet that is magnetized along an axis of the magnet (e.g., lengthwise axis, an axis that extends through the center of the magnets length or width), an axially magnetized element, or an electromagnet that can be rotated, or activated, to achieve rotation of a rotatable member. While the element exterior to the housing has been described as being rotated about the first lengthwise axis 37 of the first passageway 36, an element exterior to the housing can be rotated about any suitable axis. For example, an element exterior to the housing can be rotated about an axis that is parallel to the first lengthwise axis of a first passageway, an axis that is disposed at an angle to the first lengthwise axis of a first passageway, an axis that is coaxial with the first lengthwise axis of a first passageway to produce rotation in a rotatable member, and any other axis considered suitable for a particular embodiment.

In use, the threaded engagement between the rotatable member 14 and the housing 12 causes the rotatable member 14 to translate in the axial direction, along the first lengthwise axis 37 of the first passageway 36, when the second magnetic field 60 is applied to the first magnetic field 58 and is rotated about the first lengthwise axis 37. The direction of translation of the rotatable member 14 will depend on the direction of rotation of the second magnetic field 60. For example, when the second magnetic field 60 is rotated in a first direction relative to the housing 12, the rotatable member 14 moves from the first position toward the second position by translating along the length of the first passageway 36 toward the bottom member 28, shown by arrow 49 illustrated in FIG. 3B, and applies pressure on the membrane 18 such that the membrane 18 is moved toward the body 40 of the bottom member 28. When a vessel is disposed within the second passageway 46, the membrane 18 contacts the vessel when the rotatable member 14 is in the second position. Alternatively, when the second magnetic field 60 is rotated in a second direction relative to the housing 12 that is opposite, or substantially opposite, that of the first direction, the rotatable member 14 moves from the second position toward the first position by translating along the length of the first passageway 36 away from the bottom member 28, shown by arrow 51 in FIG. 3A, to release pressure from the membrane 18 such that the membrane is moved away from the body 40 of the bottom member 28 and returns to its original configuration, or a configuration substantially similar to its original configuration. When a vessel is disposed within the second passageway 46, the membrane 18 contacts the vessel when the rotatable member 14 is in the first position. Alternatively, a membrane can be free of contact with a vessel when a rotatable member is in the first position when the vessel is disposed within the second passageway of a housing.

Figure 8A:
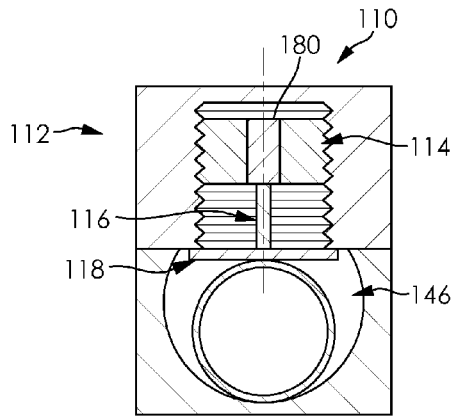
FIG. 8A is a sectional view of the gating device illustrated in FIG. 6 taken along the lengthwise axis of the housing. The gating device is assembled and in a first configuration. A portion of a vessel is disposed within the second passageway of the gating device.
Figure 8B:
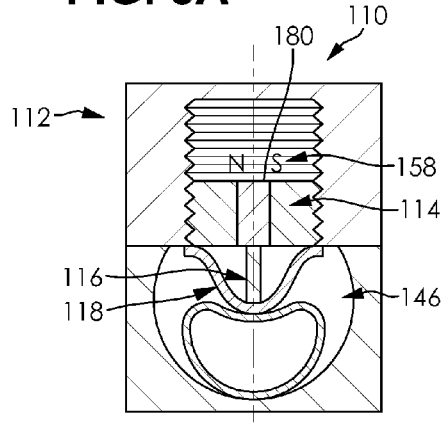
FIG. 8B illustrates the vessel and gating device shown in FIG. 8A. The gating device is in a second configuration.

When a vessel that defines a lumen is disposed within a second passageway defined by a housing of a magnetically actuated gating device, such as those described herein, the cross-sectional area of the lumen defined by the vessel can be manipulated and based on the position of a rotatable member. Movement of a rotatable member from a first position to a second position reduces the cross-sectional area of the lumen defined by the vessel and movement of the rotatable member from the second position to the first position increases the cross-sectional diameter of the lumen defined by the vessel. For example, with respect to magnetically actuated gating device 10, the lumen defined by a vessel that is disposed within the second passageway 46 has a first cross-sectional area when the rotatable member 14 is in the first position and has a second cross-sectional area when the rotatable member 14 is in the second position. The second cross-sectional area is less than the first cross-sectional area. For example, the second cross-sectional area can be equal to, or substantially equal to, 0.00 millimeters such that the lumen defined by the vessel is completely closed to fluid flow. Alternatively, the second cross-sectional area can be equal to, or substantially equal to, ¾ of the first cross-sectional area, ½ of the first cross-sectional area, ¼ of the first cross-sectional area, and any other fraction of the first cross-sectional area considered suitable for a particular embodiment. FIG. 8A illustrates a vessel disposed within a magnetically actuated gating device 110, as described in more detail herein, in which the rotatable member 114 is in the first position and the vessel has a first cross-sectional area. FIG. 8B illustrates the vessel disposed within the magnetically actuated gating device 110 in which the rotatable member 114 is in the second position and the vessel has a second cross-sectional area that is less than the first cross-sectional area. Reducing the cross-sectional area of the lumen defined by a vessel increases the fluidic resistance through the portion of the vessel disposed within a magnetically actuated gating device and produces a decrease in the flow rate through the portion of the vessel disposed within the magnetically actuated gating device and the flow rate through the portion of the vessel positioned downstream of the magnetically actuated gating device. Thus, the magnetically actuated gating devices described herein provide a mechanism for externally controlling the patency of a vessel, the flow rate through the portion of the vessel disposed within a magnetically actuated gating device, and the flow rate through the portion of the vessel positioned downstream of the magnetically actuated gating device. When a vessel is disposed within a magnetically actuated gating device, such as those described herein that include threaded components, the position of the rotatable member can be maintained without any external forces as a result of the direct or indirect (e.g., via membrane) pressure being applied by the vessel on the rotatable member.

While the compression member 16 has been illustrated as an element that compresses a vessel via the membrane 18 via axial movement of the rotatable member 14, a compression member can comprise any suitable structure, element, or feature capable of reducing the diameter of a lumen defined by a vessel, or capable of closing a lumen defined by a vessel. Skilled artisans will be able to select a suitable compression member to include in a magnetically actuated gating device according to a particular embodiment based on various considerations, including the treatment intended to be performed.

While a magnetically actuated gating device 10 has been described, FIG. 3B also illustrates a magnetically actuated gating system that comprises a magnetically actuated gating device 10 and an element 61 that is free of attachment, and disposed exterior, to the magnetically actuated gating device 10. In the illustrated embodiment, the element 61 produces a magnetic field that, when rotated and applied to the rotatable member 14, produces rotational motion in the rotatable member 14 about the lengthwise axis of the first passageway 36, as described herein. A magnetically actuated system can include any suitable magnetically actuated gating device according to an embodiment, such as magnetically actuated gating device 10, magnetically actuated gating device 110, magnetically actuated gating device 210, magnetically actuated gating device 310, magnetically actuated gating device 510, magnetically actuated gating device 610, magnetically actuated gating device 710, magnetically actuated gating device 910, variations thereof, and any other gating device considered suitable for a particular embodiment. In addition, a magnetically actuated system can include any suitable element, component, or device that is configured to, capable of producing, or that produces a magnetic field such as a magnet, a permanent magnet, an electromagnet, a rotating electromagnet, and any other element, device, and/or system considered suitable for a particular embodiment. For example, an element having a magnetic field and positioned exterior to the housing can comprise a diametrically magnetized element, a diametrically magnetized cylindrically shaped permanent magnet that is magnetized along an axis of the magnet (e.g., lengthwise axis, an axis that extends through the center of the magnets length or width), an axially magnetized element, a bar magnet, or an electromagnet that can be rotated, or activated, to achieve rotation of a rotatable member. Movement of an exterior element having a magnetic field can be accomplished using any suitable technique and/or method of producing rotation. Example techniques and methods of producing rotation considered suitable to produce rotation in an element having a magnetic field include using a drill, such as a surgical drill, on which the element is attached, manipulating the element by hand, and any other technique and/or method considered suitable for a particular embodiment.

FIG. 4 illustrates an alternative rotatable member 14' and compression member 16' suitable for use in a magnetically actuated gating device according to an embodiment. The rotatable member 14' is similar to the rotatable member 14 illustrated in FIGS. 1, 2, 3A, and 3B and described above, except as detailed below. The compression member 16' is similar to the compression member 16 illustrated in FIGS. 1, 2, 3A, and 3B and described above, except as detailed below. The rotatable member 14' comprises a first end 50', a second end 52', and a body 54' that defines threads 56' and the compression member 16' has a first end 62', a second end 64', and a body 66'.

The rotatable member 14' includes an axle 74' that extends from the second end 52' of the rotatable member 14' toward the first end 50' of the rotatable member 14'. The second end 52' of the rotatable member 14' is enlarged relative to the portion of the axle 74' disposed between the first end 50' and the second end 52'. This structural configuration provides a mechanism to rotatably attach the rotatable member 14' to the compression member 16', as described below.

The compression member 16' is formed as a partial cylinder and has a body 66' that defines a notch 78' that is sized and configured to receive the enlarged second end 52' of the rotatable member 14' and a portion of the axle 74'. The notch 78' extends into the body 66' of the compression member 16' from a first side of the compression member 16' and toward a second side of the compression member 16' to a blind end 79' and from the first end 62' toward the second end 64'. Thus, the notch 74' extends along a portion of the diameter of the compression member 16'.

When assembled, the enlarged second end 52' of the rotatable member 14' is positioned within the notch 78' and is advanced toward the blind end 79' of the notch 74'. Subsequent to the enlarged second end 52' being positioned within the notch 78', the opening created by the notch 78' on the side of the rotatable member 14' is closed to prevent the rotatable member 14' from becoming free of the compression member 16'. This can be accomplished using any suitable structure or material, such as an adhesive.

In use, as the rotatable member 14' is moved between its first and second positions, the compression member 16' is configured to maintain its position, or substantially maintain its position, relative to the housing (not shown) such that it does not rotate relative to the housing or membrane. This provides a mechanism to prevent damage to the membrane, or, in embodiments in which a membrane has been omitted, to prevent damage to the vessel.

Figure 5:
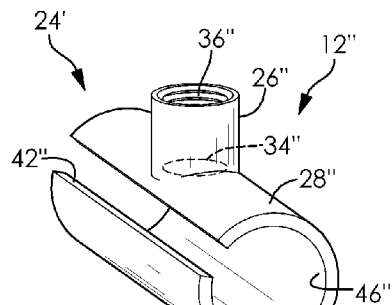
FIG. 5 is a perspective view of an example alternative housing.

FIG. 5 illustrates an alternative housing 12" suitable for use in a magnetically actuated gating device according to an embodiment. The housing 12" is similar to the housing 12 illustrated in FIGS. 1, 2, 3A, and 3B and described above, except as detailed below. The housing 12" comprises a first end 22", a second end 24", a top member 26", and a bottom member 28".

The top member 26" and the bottom member 28" are integrally formed and each of the top member 26" and bottom member 28" is cylindrical. In the illustrated embodiment, the slit 42" of the bottom member 28" is positioned such that it is not in communication with the first passageway 36" defined by the top member 26" and the second opening 34" defined by the top member 26" is in communication with the second passageway 46" defined by the bottom member 28". This structural arrangement provides a mechanism for passing a vessel into the second passageway 46" through the slit 42" without having to form the housing 12" of two separate members.

Figure 7A:
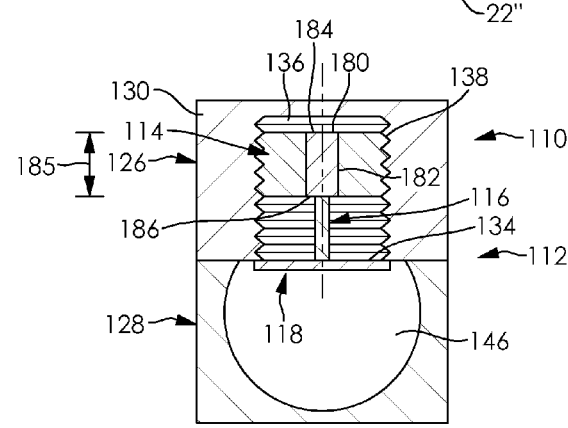
FIG. 7A is a sectional view of the gating device illustrated in FIG. 6 taken along the lengthwise axis of the housing. The gating device is assembled and in a first configuration.
Figure 6:
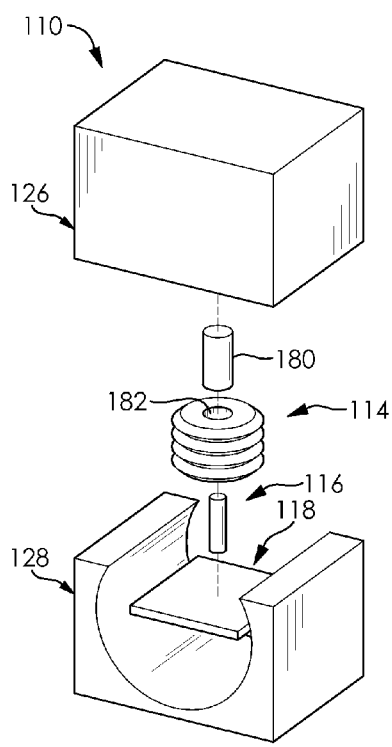
FIG. 6 is an exploded perspective view of another example embodiment of a gating device.
Figure 7B:
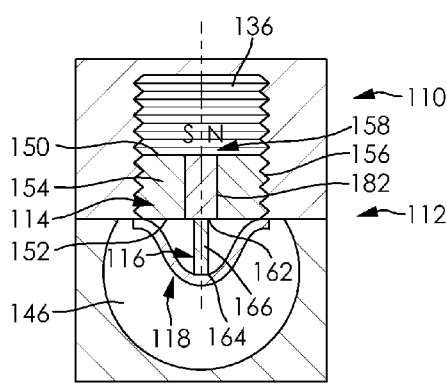
FIG. 7B is a sectional view of the gating device illustrated in FIG. 6 taken along the lengthwise axis of the housing. The gating device is assembled and in a second configuration.

FIGS. 6, 7A, 7B, 8A, and 8B illustrate another example embodiment of a magnetically actuated gating device 110. Magnetically actuated gating device 110 is similar to magnetically actuated gating device 10 illustrated in FIGS. 1, 2, 3A, and 3B and described above, except as detailed below. The magnetically actuated gating device 110 comprises a housing 112, a rotatable member 114, a compression member 116, and a membrane 118. The magnetically actuated gating device 110 is moveable between a first configuration, as shown in FIGS. 7A and 8A, and a second configuration, as shown in FIGS. 7B and 8B.

In the illustrated embodiment, alternative to the rotatable member 114 having a first magnetic field, the magnetically actuated gating device 110 includes a magnetically actuated member 180 that has a first magnetic field 158, as shown in FIG. 7B. In addition, the body 130 of the top member 126 defines a blind first passageway 136 that extends from an opening 134 defined on a surface that faces the bottom member 128 and into the body 130 of the top member 126. The threads 138 defined by the body 130 of the top member 126 extend from the opening 134 and away from the bottom member 128.

In the illustrated embodiment, the body 154 of the rotatable member 114 defines threads 156 and a passageway 182. The threads 156 extend from the first end 150 to the second end 152 of the rotatable member 114. The passageway 182 extends from the first end 150 to the second end 152 of the rotatable member 114 and is sized and configured to receive the magnetically actuated member 180, as described in more detail herein. While the body 154 of the rotatable member 114 has been illustrated as defining a passageway 182, alternative embodiments can include a rotatable member that defines a recess that extends into the body of a rotatable member (e.g., from the first end and toward the second end, from the second end and toward the first end, from a first side of a rotatable member and toward a second side of the rotatable member, from a second side of a rotatable member and toward a first side of the rotatable member) that is sized and configured to receive a portion, or the entirety, of a magnetically actuated member. Alternatively, a rotatable member can omit the inclusion of a passageway or a recess and a magnetically actuated member can be attached to a surface of a rotatable member using any suitable method or technique, such as using adhesive, fusing, welding, friction fit attachments, and any other technique or method considered suitable for a particular embodiment.

The magnetically actuated member 180 has a first magnetic field 158, a first end 184, a second end 186, a length 185, and a diameter 187 and is disposed within the passageway 182 defined by the rotatable member 114. The magnetically actuated member 180 is adhesively attached to the rotatable member 114. The length 185 of the magnetically actuated member 180 extends from its first end 184 to its second end 186 and is equal to the length of the rotatable member 114 and the passageway 182 defined by the rotatable member 114. In addition, the diameter 187 of the magnetically actuated member 180 is equal to the diameter of the passageway 182 defined by the rotatable member 114. However, alternative embodiments can include a magnetically actuated member that has a length and/or diameter that is equal to, substantially equal to, less than, or greater than, the length and/or diameter of a rotatable member, a passageway defined by a rotatable member, and/or of a recess defined by a rotatable member.

The first magnetic field 158 is similar to the first magnetic field 58 described above with respect to the rotatable member 14 and can be used to move the rotatable member 114 between the first and second positions as described above with respect to magnetically actuated gating device 10. In the illustrated embodiment, the first magnetic field 158 is created across the diameter of the magnetically actuated member 180 such that the magnetically actuated member 180 is diametrically magnetized. Attachment of the magnetically actuated member 180 to the rotatable member 114 provides a mechanism to transfer rotational forces applied to the magnetically actuated member 180 to the rotatable member 114 when a second magnetic field is applied to the first magnetic field 158. While the magnetically actuated member 180 has been described as adhesively attached to the rotatable member 114, a magnetically actuated member can be attached to a rotatable member using any suitable technique or method of attachment, such as fusing, welding, friction fit attachments, and any other technique or method considered suitable for a particular embodiment, such as those described herein. Any of the magnetically actuated gating devices described herein can include a rotatable member or a combination of a rotatable member and a magnetically actuated member.

The magnetically actuated member 180 can be formed of any suitable material and can be fabricated using any suitable method or technique. Skilled artisans will be able to select a suitable material to form a magnetically actuated member and a suitable method or technique to fabricate a magnetically actuated member according to a particular embodiment based on various considerations, including the material(s) that forms a rotatable member included in a magnetically actuated gating device of which the magnetically actuated member is a component. Example materials considered suitable to form a magnetically actuated member include biocompatible materials, materials that can be made biocompatible, materials that produce a magnetic field, materials that can be made magnetic, materials that can be magnetized, materials that form permanent magnets, ferromagnetic materials, ferrite, permanent magnets, rare-earth permanent magnets, metals such as stainless steel, titanium, nickel-titanium alloys (e.g., Nitinol), polymers, Pebax, nylon, polyethylene, polyurethane, silicone, combinations of the materials described herein, and any other material considered suitable for a particular application. Example methods and techniques considered suitable to fabricate a magnetically actuated member include extrusion processes, molding processes, injection molding processes, casting processes, and any other method or technique considered suitable for a particular embodiment. For example, a magnetically actuated member included in a magnetically actuated gating device can be formed of a material that has been magnetized across its diameter, along an axis that is orthogonal to the lengthwise axis of the magnetically actuated member, such that the magnetically actuated member is a diametrically magnetized element. In embodiments in which the magnetically actuated member is diametrically magnetized, the magnetically actuated member has a first magnetic pole on a first side and a second magnetic pole on a second side that is opposably facing the first side. The first magnetic pole is different than the second magnetic pole. Alternatively, a magnetically actuated member can be magnetized such that it forms a series of magnetic north and south poles that alternate around the lengthwise axis and/or the circumference of the magnetically actuated member.

In the illustrated embodiment, the compression member 116 has a first end 162, a second end 164, a body 166, as shown in FIG. 7B, and is formed of a ferromagnetic material such that it is axially magnetized. Thus, the compression member 116 has a first magnetic pole at the first end 162 and a second magnetic pole at the second end 164 that is different than the first magnetic pole. This structural configuration provides a mechanism to releasably magnetically attach the compression member 116 to the second end 186 of the magnetically actuated member 180. The second end 164 of the compression member 116 is attached to the membrane 118 using adhesive such that during use the compression member 116 is fixed relative to the membrane 118. This arrangement prevents the compression member 116 from rotating during use and allows the rotatable member 114 and the magnetically actuated member 180 to rotate relative to the housing 112. While the compression member 116 has been described as being adhesively attached to the membrane 118, alternative embodiments can include a compression member that is free of attachment to a membrane or attached to a membrane using any other suitable technique or method of attachment, such as fusing, welding, and any other technique or method considered suitable for a particular embodiment, such as those described herein.

In use, when the first end 150 of the rotatable member 114 is rotatably advanced toward the second passageway 146 defined by the housing 112, the compression member 116 applies a force on the membrane 118 that is directed into the second passageway 146. When the first end 150 of the rotatable member 114 is rotatably advanced away from the second passageway 146 defined by the housing 112, the compression member 116 removes the force on the membrane 118 that is directed into the second passageway 146.

Figure 9:
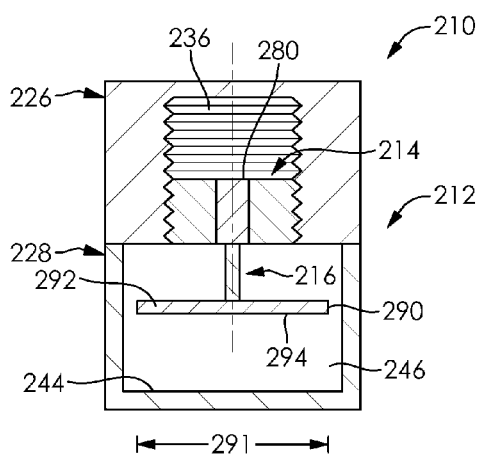
FIG. 9 is a sectional view of another example embodiment of a gating device taken along the lengthwise axis of the housing. The gating device is in a second configuration.

FIG. 9 illustrates another example embodiment of a magnetically actuated gating device 210. Magnetically actuated gating device 210 is similar to magnetically actuated gating device 110 illustrated in FIGS. 6, 7A, 7B, 8A, and 8B and described above, except as detailed below. The magnetically actuated gating device 210 comprises a housing 212, a rotatable member 214, a compression member 216, and a magnetically actuated member 280. The magnetically actuated gating device 210 is moveable between a first configuration, not shown, and a second configuration, as shown in FIG. 9.

In the illustrated embodiment, the magnetically actuated gating device 210 includes a plate 290 alternative to a membrane (e.g., membrane 218). In addition, the first passageway 236 defined by the top member 226 is in fluid communication with the second passageway 246 defined by the bottom member 228 and the bottom member 228 of the housing 212 defines a recess 244 that has a rectangular cross-sectional configuration.

In the embodiment illustrated, the plate 290 is attached to the compression member 216 and has a length 291 and a body 292 that defines a contact surface 294. The plate 290 can be attached to a compression member 216 using any suitable technique or method of attachment, such as using adhesive, fusing, or welding. The length 291 of the plate 290 is substantially equal to the length of the second passageway 246 that extends from a first side of the second passageway 246 to a second side of the second passageway 246 on an axis that is orthogonal to the second lengthwise axis of the second passageway 246. However, alternative embodiments can include a plate that has a length that is equal to, or less than, the length of a second passageway, 50% of the length of a second passageway, 75% of the length of a second passageway, 99% of the length of a second passageway, and any other length considered suitable for a particular embodiment. While the plate 290 has been illustrated as being attached to the compression member 216, alternative embodiments can include a compression member or rotatable member that is rotatably attached to a plate such that the compression member or rotatable member can rotate relative to the plate.

While the plate 290 has been illustrated as having a rectangular cross-sectional configuration and a substantially straight contact surface 294 that is intended to contact a vessel when disposed within the second passageway 246, a plate can have any suitable cross-sectional configuration and/or define any suitable contact surface. Example cross-sectional configurations considered suitable for a plate include cross-sectional configurations that are square, circular, semi-circular, spherical, semi-spherical, and any other cross-sectional configuration considered suitable for a particular embodiment. Example structural arrangements for a contact surface considered suitable include contact surfaces that are straight, curved, crescent shaped, and any other structural arrangement considered suitable for a particular embodiment.

Optionally, the magnetically actuated gating device 210 can include a membrane, such as the membrane 118 illustrated in FIGS. 6, 7A, 7B, 8A, and 8B that is disposed between the plate 290 and the bottom member 228 and attached to the top member 226, or a combination of the top member 226 and the bottom member 228. For example, a portion of a non-compliant balloon can be attached to the top member 226 such that it seals the first passageway 236 and contacts a vessel when a vessel is disposed within the second passageway 246.

Figure 10A:
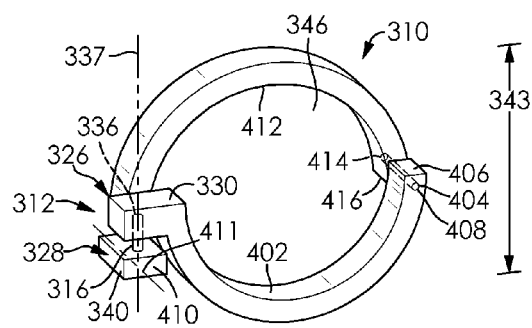
FIG. 10A is a perspective view of another example embodiment of a gating device. The gating device is in a first configuration.
Figure 10B:
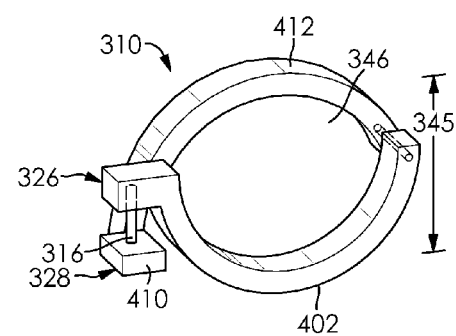
FIG. 10B is a perspective view of the gating device illustrated in FIG. 10A. The gating device is in a second configuration.

FIGS. 10A and 10B illustrate another example embodiment of a magnetically actuated gating device 310. Magnetically actuated gating device 310 is similar to magnetically actuated gating device 110 illustrated in FIGS. 6, 7A, 7B, 8A, and 8B and described above, except as detailed below. The magnetically actuated gating device 310 comprises a housing 312, a rotatable member (not shown), a compression member 316, and a magnetically actuated member (not shown). The magnetically actuated gating device 310 is moveable between a first configuration, as shown in FIG. 10A, and a second configuration, as shown in FIG. 10B.

In the illustrated embodiment, the body 330 of the top member 326 defines a first passageway wall 402 and an aperture 404. The first passageway wall 402 extends outward and away from the first lengthwise axis 337 of the first passageway 336 to an end 406. In the illustrated embodiment, the first passageway wall 402 forms a partial circle. The aperture 404 is defined on the first passageway wall 402 near the end 406 of the first passageway wall 404 and is sized and configured to receive a portion of a pin 408.

In the illustrated embodiment, alternative to a slit (e.g., slit 142) and a recess (e.g., recess 144) the body 340 of the bottom member 328 defines a plate 410, a second passageway wall 412, and an aperture 414. The plate 410 has a lengthwise axis 411 that extends through its length and orthogonally to the first lengthwise axis 337 of the first passageway 336. The plate 410 is moveable between a first position, as illustrated in FIG. 10A, and a second configuration, as illustrated in FIG. 10B and described in more detail below. The plate 410 is in the first position when the rotatable member is in the first position and is in the second position when the rotatable member is in the second position. The second passageway wall 412 extends outward and away from the lengthwise axis 411 of the plate 410 to an end 416. In the illustrated embodiment, the second passageway wall 412 is formed as a partial circle. The aperture 414 is defined on the second passageway wall 412 near the end 416 of the second passageway wall 412 and is sized and configured to receive a portion of the pin 408.

The first passageway wall 402 and the second passageway wall 412 cooperatively define the second passageway 346, which is sized and configured to receive a portion of a vessel.

The pin 408 is disposed within the aperture 404 defined by the body 330 of the top member 326 and the aperture 414 defined by the body 340 of the bottom member 328. The pin 408 provides a hinged attachment between the first passageway wall 402 and the second passageway wall 412.

While each of the first passageway wall 402 and the second passageway wall 412 has been illustrated and forming a partial circle, a passageway wall can define any suitable structural configuration. Skilled artisans will be able to select a suitable structural configuration for a passageway wall to define according to a particular embodiment based on various considerations, including the intended use of the magnetically actuated gating device. Example structural configurations considered suitable for a passageway wall to define include partial ovals, ellipses, crescents, and any other structural configuration considered suitable for a particular embodiment.

In use, the plate 410 contacts the top member 326 of the housing 312 when the rotatable member is in the first position and is free of contact of the top member 326 of the housing 312 when the rotatable member is in the second position. Thus, the plate 410 is disposed a first distance from the top member 326 of the housing 312 when the rotatable member is in the first position and is disposed a second distance from the top member 326 of the housing 312 when the rotatable member is in the second position. The second distance is greater than the first distance. The second passageway 346 has a first diameter 343 when the plate 410 is in the first position and a second diameter 345 when the plate 410 is in the second position. The second diameter 345 is less than the first diameter 343. As the rotatable member 314 is moved from the first position toward the second position, the plate 410 moves away from the top member 326 of the housing 312 and the diameter of the second passageway 346 decreases in size. As the rotatable member 314 is moved from the second position toward the first position, the plate 410 moves toward the top member 326 of the housing 312 and the diameter of the second passageway 346 increases in size.

FIGS. 11A and 11B illustrate another example embodiment of a magnetically actuated gating device 510. Magnetically actuated gating device 510 is similar to magnetically actuated gating device 10 illustrated in FIGS. 1, 2, 3A, and 3B and described above, except as detailed below. The magnetically actuated gating device 510 comprises a housing 512, a rotatable member 514, a compression member 516, and a cap 520. The magnetically actuated gating device 510 is moveable between a first configuration, as shown in FIG. 11A, and a second configuration, as shown in FIG. 11B.

In the illustrated embodiment, the body 530 of the top member 526 defines a first opening 532 that has a first diameter 533 and a second opening 534 that has a second diameter 535 that is less than the first diameter 533. The first diameter 533 extends along a first portion of the first passageway 536 that extends from the first opening 532 toward the second opening 534 and the second diameter 535 extends along a second portion of the first passageway 536 that extends from the second opening 534 toward the first opening 532. This configuration defines a shoulder 539 that prevents the rotatable member 514 from being advanced into the second passageway 546 through the first passageway 536.

The body 540 of the bottom member 528 defines a recess 544 that has a rectangular cross-sectional configuration that is sized and configured to receive a portion of a vessel and the compression member 516. As illustrated in FIG. 11B, the first lengthwise axis 537 of the first passageway 536 is offset from the second lengthwise axis 547 of the second passageway 546 such that they do no intersect.

The rotatable member 514 has an outside diameter that extends from the first end 550 to the second end 552 and omits the inclusion of threads (e.g., threads 56) such that the rotatable member 514 can freely rotate within the first passageway 536. Thus, the rotatable member 514 has a constant outside diameter along its length. Alternative embodiments, however, can include a rotatable member that does not have a constant outside diameter along its length and/or a diameter that is based on the inside diameter of the passageway within which the rotatable member is disposed. The rotatable member 514 is moveable between a first position and a second position. In the first position, a first side of the rotatable member 514 is directed toward a first side of the first passageway 536. In the second position, a second side of the rotatable member 514 is direct toward the first side of the first passageway 536. Thus, movement of the rotatable member 514 from its first position to its second position, and vice versa, is achieved by rotating the rotatable member 514 180 degrees about its lengthwise axis.

In the illustrated embodiment, the compression member 516 has a first end 562, a second end 564, and a body 566 that defines a shaft 568 and a projection 570. In the illustrated embodiment, the compression member 516 is not formed of a ferromagnetic material. However, alternative embodiments can include a compression member that is formed of a ferromagnetic material. The first end 562 of the compression member 516 is attached to the second end 552 of the rotatable member 514 such that it rotates with the rotatable member 514 when a second magnetic field (e.g., alternating magnetic field, rotating magnetic field) is applied to the rotatable member 514. The compression member 516 extends from the first end 562 through the second opening 534 of the top member 526 to the second end 564.

The shaft 568 has a first outside diameter 567. The projection 570 has a second outside diameter 571 and a third outside diameter 573. Each of the second outside diameter 571 and the third outside diameter 573 of the projection 570 is greater than the first outside diameter 567 of the shaft 568. In the illustrated embodiment, the projection 570 extends from the second end 564 of the compression member 516 toward the first end 564 and is formed as an elliptic cylinder such that the second outside diameter 571 is less than the third outside diameter 573. However, alternative embodiments can include a projection that is disposed between the first end and the second end of a compression member and/or that comprises any suitable geometric shape that has a first diameter on a first axis and a second, different, diameter on a second axis that is disposed orthogonal to the first axis. In the illustrated embodiment, the compression member 516 has a first position, shown in FIG. 11A, in which the second outside diameter 571 of the projection 570 is disposed on a plane that extends orthogonal to the second lengthwise axis 547 of the second passageway 546 and a second position, shown in FIG. 11B, in which the third outside diameter 573 of the projection 570 is disposed on a plane that extends orthogonal to the second lengthwise axis 547.

In use, the compression member 516 is in its first position when the rotatable member 514 is in its first position and the compression member 516 is in the second position when the rotatable member 514 is in the second position. Movement of the rotatable member 514 and the compression member 516 is achieved by applying a second magnetic field to the first magnetic field of the rotatable member 514, as described herein.

FIGS. 12A and 12B illustrate another example embodiment of a magnetically actuated gating device 610. Magnetically actuated gating device 610 is similar to magnetically actuated gating device 510 illustrated in FIGS. 11A and 11B and described above, except as detailed below. The magnetically actuated gating device 610 comprises a housing 612, a rotatable member 614, and a compression member 616. The magnetically actuated gating device 610 is moveable between a first configuration, as shown in FIG. 12A, and a second configuration, as shown in FIG. 12B.

In the illustrated embodiment, the projection 670 is formed as a circular cylinder that is disposed between the first end 662 and the second end 664 of the compression member 616. In addition, the projection 670 has a lengthwise axis 675 and is attached to the shaft 668 such that the attachment between the shaft 668 and the projection 670 is located on an axis that is not coaxial with the lengthwise axis 675 of the projection 670. Thus, the shaft 668 is attached to the projection 670 off-center. This configuration provides a compression member 616 that has a first position, shown in FIG. 12A, in which a first cross section of the circular cylinder is disposed on a plane that extends orthogonal to the second lengthwise axis 647 and a second position, shown in FIG. 12B, in which a second cross section of the circular cylinder is disposed on a plane that extends orthogonal to the second lengthwise axis 647. The first cross section is the same as the second cross section. However, due to the off-set nature of the attachment of the shaft 668 to the projection 670, the projection 670 is disposed a first distance from the second lengthwise axis 647 when the rotatable member 614 is in the first position and is disposed a second distance from the second lengthwise axis 647 when the rotatable member is in the second position. The first distance is different than the second distance. In the illustrated embodiment, the first distance is greater than the second distance.

FIGS. 13, 14A, and 14B illustrate another example embodiment of a magnetically actuated gating device 710. Magnetically actuated gating device 710 is similar to magnetically actuated gating device 110 illustrated in FIGS. 6, 7A, 7B, 8A, and 8B and described above, except as detailed below. The magnetically actuated gating device 710 comprises a housing 712, a rotatable member 714, a compression member 716, and a magnetically actuated member 780. The magnetically actuated gating device 710 is moveable between a first configuration, as shown in FIG. 14A, and a second configuration, as shown in FIG. 14B.

In the illustrated embodiment, the top member 726 of the housing 712 defines a first passageway 736 that extends from a first opening 732 to a second opening 734. In addition, the top member 726 defines a first aperture 802 and a second aperture 804. The first passageway 736 is sized and configured to receive a portion of the compression member 716. Each of the first aperture 802 and second aperture 804 is sized and configured to receive a portion of a pin 806. Alternative embodiments, however, can omit the inclusion of a first aperture, a second aperture, and/or a pin.

In the illustrated embodiment, the body 740 of the bottom member 728 defines a slit 742, a recess 744, a groove 810, a mounting surface 812, a wall 814, a passageway 816, a recess 818, and a projection 820. When assembled, as shown in FIGS. 14A and 14B, the top member 726 and the bottom member 728 are releasably attached to one another such that the recess 744 and a portion of the body 730 of the top member 726 cooperatively define the second passageway 746 that is sized and configured to receive a vessel.

The groove 810 extends into the body 740 of the bottom member 728 and is sized and configured to receive a portion of the compression member 716. In the illustrated embodiment, the groove 810 is defined on the wall of the bottom member 728 that defines the recess 744 such that it is aligned with the first passageway 736 defined by the top member 726 and the passageway 816 defined by the bottom member 728. This configuration provides structure that positions the compression member 716 within the groove 810 when the rotatable member 714 is in the first configuration and prevents obstructing the second passageway 746.

The mounting surface 812 extends from the second lengthwise axis 747 of the second passageway 746 and is sized and configured to receive the rotatable member 714, a portion of the compressible member 716, and magnetically actuated member 780. The wall 814 extends outward and away from the mounting surface 812 and along a portion of the perimeter of the mounting surface 812. The wall 814 provides a mechanism for maintaining the position of the compression member 716 during use. The passageway 816 extends through the body 740 of the bottom member 728 and provides access between the second passageway 746 and the mounting surface 812. The passageway 816 is sized and configured to receive a portion of the compression member 716.

The recess 818 is defined on the mounting surface 812 and is sized and configured to receive a portion of the magnetically actuated member 780. The recess 818 has a first inside diameter 817 and a second inside diameter 819. The first inside diameter 817 is less than the second inside diameter 819. This structural configuration provides a mechanism for rotatably attaching the magnetically actuated member 780 to the bottom member 728 via a snap fit configuration.

The projection 820 extends from the mounting surface 812 and is sized and configured to interact with the projection 757 of the rotatable member 714, as described in more detail herein. This configuration provides a mechanical stop to rotation of the rotatable member 714 during use such that the compression member 716 does not over tighten a vessel when disposed within the second passageway 746.

In the illustrated embodiment, the rotatable member 714 has a lengthwise axis 751, as shown in FIG. 14B, a first end 750, a second end 752, an outside diameter 753, and a body 754 that defines a first passageway 755, a second passageway 756, and a projection 757. The first passageway 755 extends from the first end 750 to the second end 752 and is sized and configured to receive a portion of magnetically actuated member 780, as described in more detail herein. The second passageway 756 extends between the first passageway 755 and the outer edge of the rotatable member 714. The second passageway 756 is sized and configured to receive a portion of the compression member 716. The projection 757 extends from the outer edge of the rotatable member 714 and away from the lengthwise axis 751 of the rotatable member 714. The projection 757 is sized and configured to interact with the projection 820 defined by the housing 712 to prevent the projection 757 of the rotatable member 714 from advancing beyond the projection 820 defined by the housing 712 during use. This configuration provides a mechanism for preventing overtightening of a vessel during movement of the compression member 716 to the second position.

In the illustrated embodiment, the compression member 716 comprises an elongate member that has a first end 762, a second end 764, and a body 766 that has an outside diameter 767. The first end 762 is attached to the top member 726 of the housing 712 within first passageway 736 and the second end 764 is attached to the rotatable member 714 within the second passageway 756 defined by the rotatable member 714. The pin 806 is disposed through the first aperture 802, the first passageway 736, the second aperture 804, and the compression member 716 to achieve attachment of the compression member 716 to the top member 726. The compression member 716 extends from the first end 762 into the second passageway 746 through the first opening 816 defined by the bottom member 728 of the housing 712 and into the second passageway 756 defined by the rotatable member 714. The second end 764 of the compression member 716 is attached to the rotatable member 714 using an adhesive. However, other techniques or methods of attachment can be used to attach a compression member to a housing and/or a rotatable member, such fusing, welding, and any other technique or method considered suitable for a particular embodiment, such as those described herein.

In the illustrated embodiment, the compression member 716 is formed of a polymer and is relatively more flexible than the material that forms the housing 712 such that the compression member 716 can bend relative to the housing 712 during use and in response to movement of the rotatable member 714 between its first and second positions. In the illustrated embodiment, the compression member 716 is an off the shelf surgical band configured to contact a vessel and move between first and second positions, as described herein. However, alternative embodiments can include a compression member formed of any suitable material, such as metal, and any other material considered suitable for a particular embodiment, such as those described herein.

The magnetically actuated member 780 has a first end 784, a second end 786, a length 785, a first outside diameter 787, and a second outside diameter 789. The first outside diameter 787 extends from the first end 784 toward the second end 786. The second outside diameter 789 extends from the second end 786 toward the first end 784. The first outside diameter 787 is less than the second outside diameter 789 and is less than the second inside diameter 819 of the recess 818 defined by the bottom member 728. The second outside diameter 789 is greater than the first inside diameter 817 of the recess 818 defined by the bottom member 728. In the illustrated embodiment, the magnetically actuated member 780 is disposed within the first passageway 755 defined by the rotatable member 714 and is rotatably attached to the housing 712 within the recess 818 defined by the bottom member 728 via a snap fit attachment. The magnetically actuated member 780 is adhesively attached to the rotatable member 714 such that movement of the magnetically actuated member 780 results in movement of the rotatable member 714.

In use, when a second magnetic field is applied to the first magnetic field of the magnetically actuated member 780, the rotatable member 714 rotates such that the compression member 716 moves from its first position in which it is disposed a first distance from the second lengthwise axis 747, as shown in FIG. 14A, to its second position in which it is disposed a second distance from the second lengthwise axis 747, as shown in FIG. 14B. The second distance is less than the first distance. When a vessel is disposed within the second passageway 746, movement of the compression member 716 from the first position to the second position results in a circumferential compressive force being applied to the vessel. When the second magnetic field is removed from the first magnetic field 758 of the magnetically actuated member 780, the rotatable member 714 returns to its first position. Any suitable structure can be used to maintain the rotatable member 714 in the second position and skilled artisans will be able to select a suitable structure to maintain the position of a rotatable member in the second position according to a particular embodiment based on various considerations, including the arrangement of a housing on which a rotatable member is disposed. Example structures considered suitable include positioning an armband that includes a magnet on a patient's forearm that is disposed over a magnetically actuated gating device (e.g., the magnetically actuated member 780). The magnet has a first pole that is opposite the first pole of a magnetically actuated member and a second pole that is opposite the second pole of the magnetically actuated member such that the magnet included on the armband maintains the position of the rotatable member when it is worn by the patient.

While the housing 712 and the magnetically actuated member 780 have been illustrated as defining a snap fit rotatable attachment, a housing and/or magnetically actuated member can define any suitable structure to accomplish rotatable attachment between the magnetically actuated member and the housing. Optionally, additional structure can be included to accomplish rotatable attachment between the magnetically actuated member and the housing. Skilled artisans will be able to select a suitable structure to include on a magnetically actuated gating device to accomplish rotatable attachment between a magnetically actuated member and a housing according to a particular embodiment based on various considerations, including the material(s) that forms the housing and/or magnetically actuated member. For example, alternative to a snap fit configuration, a housing and magnetically actuated member can define mating threaded connections that provide rotatable attachment of the magnetically actuated member to the housing. Alternatively, a rotatable member can be rotatably attached to a housing of a magnetically actuated gating device using any suitable structure, such as using a screw that has an unthreaded portion on which a rotatable member can rotate, or any other structure considered suitable for a particular embodiment, such as those described herein.

Alternative to the second end 764 of the compression member 716 being directly attached to the rotatable member 716, the second end of a compression member can be attached to a flexible member that is flexible relative to the compression member. In these alternative embodiments, the flexible member has a first end attached to the second end of the compression member and a second end attached to the rotatable member using any suitable technique or method of attachment, such as adhesive. During use, the flexible member stretches along its length and applies a force on the compression member as the rotatable member rotates about its lengthwise axis. This arrangement provides a mechanism to reduce the force applied to the compression member during use.

Optionally, the magnetically actuated gating device 710 can include a membrane disposed between the compression member 716 and the lengthwise axis 747 of the second passageway 746. For example, a portion of a non-compliant balloon can be attached to the bottom member 728 such that it is disposed over the compression member 716 and contacts a vessel when a vessel is disposed within the second passageway 746.

Figure 15:
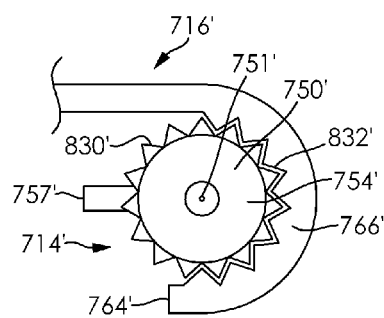
FIG. 15 is a partial top view of an example alternative rotatable member and compression member.

FIG. 15 illustrates an alternative rotatable member 714' and compression member 716' suitable for use in a magnetically actuated gating device according to an embodiment. The rotatable member 714' is similar to the rotatable member 714 illustrated in FIGS. 13, 14A, and 14B and described above, except as detailed below. The compression member 716' is similar to the compression member 716 illustrated in FIGS. 13, 14A, and 14B and described above, except as detailed below. The rotatable member 714' comprises a first end 750', a second end (not shown), and a body 754' and the compression member 716' has a first end (not shown), a second end 764', and a body 766'.

The body 754' of the rotatable member 714' defines a projection 757' and a plurality of teeth 830'. The plurality of teeth 830' is defined along the entire circumference of the main body of the rotatable member 714'. However, alternative embodiments can include a rotatable member that defines one or more teeth that extend along a portion of the circumference of the main body of a rotatable member. Each tooth of the plurality of teeth 830' extends outward and away from the lengthwise axis 751' of the rotatable member 714' and defines a first toothed geometry that corresponds to a second toothed geometry defined by a plurality of teeth 832' defined by the compression member 716', as described in more detail herein.

The body 766' of the compression member 716' defines a plurality of teeth 832' that extends from the second end 764' toward the first end and is directed toward the plurality of teeth 830' defined by the rotatable member 714'. However, alternative embodiments can include a compression member that defines one or more teeth that extend between the first end and the second end of a compression member. Each tooth of the plurality of teeth 832' extends outward and away from the lengthwise axis of the compression member 716' and defines a second toothed geometry that corresponds to a first geometry defined by a tooth of the plurality of teeth 830' defined by the rotatable member 714'.

In use, the first toothed geometry defined by each tooth of the plurality of teeth 830' interact with the second toothed geometry defined by each tooth of the plurality of teeth 832' such that a force applied to the rotatable member 714' about the lengthwise axis 751' of the rotatable member 714' is transferred to the compression member 716'. The structural arrangement and corresponding geometry of the rotatable member 714' and the compression member 716' provide a mechanism to prevent slippage between the rotatable member 714' and the compression member 716' during use.

A rotatable member and/or compression member can define any suitable toothed geometry, and skilled artisans will be able to select a suitable toothed geometry to define on a rotatable member and/or a compression member according to a particular embodiment based on various considerations, including the material(s) that forms a rotatable member and/or a compression member. For example, the cross-sectional configuration of a tooth defined by a rotatable member and/or compression member can comprise any suitable cross-sectional configuration, such as rectangular, square, triangular, trapezoidal, and any other structural configuration considered suitable for a particular embodiment.

While the rotatable member 714' has been illustrated as defining a plurality of teeth 830' and the compression member 716' has been illustrated as defining a plurality of teeth 832', a rotatable member and compression member can define any suitable number of teeth. For example, a rotatable member and/or compression member included in a magnetically actuated gating device can define one, at least one, two, a plurality, three, four, five, six, seven, and any other suitable number of teeth.

Figure 16A:
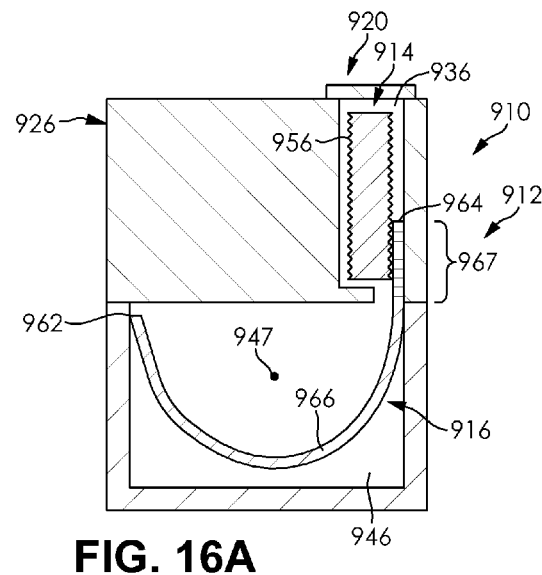
FIG. 16A is a sectional view of another example embodiment of a gating device taken along the lengthwise axis of the housing. The gating device is in a first configuration.
Figure 16B:
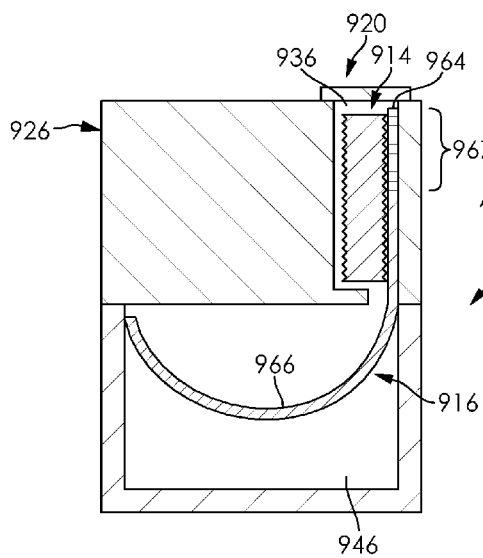
FIG. 16B illustrates the gating device shown in FIG. 16A in a second configuration.

FIGS. 16A and 16B illustrate another example embodiment of a magnetically actuated gating device 910. Magnetically actuated gating device 910 is similar to magnetically actuated gating device 510 illustrated in FIGS. 11A and 11B and described above, except as detailed below. The magnetically actuated gating device 910 comprises a housing 912, a rotatable member 914, a compression member 916, and a cap 920. The magnetically actuated gating device 910 is moveable between a first configuration, as shown in FIG. 16A, and a second configuration, as shown in FIG. 16B.

In the illustrated embodiment, the top member 926 of the housing 912 defines a first passageway 936 that is in communication with the second passageway 946 and that is sized and configured to receive the rotatable member 914 and a portion of the compression member 916, as described in more detail herein. The rotatable member 914 defines threads 956 that are configured to interact with a portion of the compression member 916 such that rotation of the rotatable member 914 moves the compression member 916 between its first and second positions. Each thread of the threads 956 is sized and configured to be partially disposed within a slot of the plurality of slots 967 defined by the compression member 916 to achieve movement of the compression member 916.

The compression member 916 comprises a first end 962, a second end 964, and a body 966 that defines a plurality of slots 967. The first end 962 is attached within the second passageway 946 defined by the bottom member 928 and the second end 964 is free of attachment to the bottom member 928 and is disposed within the first passageway 936 defined by the top member 926. Each slot of the plurality of slots 967 is sized and configured to receive a portion of a thread 956 defined by the rotatable member 914. The plurality of slots 967 are defined between the first end 962 and the second end 964 of the compression member 916 such that no slots are defined from the first end 962 of the compression member 916 to the midpoint of the compression member 916. Alternatively, the plurality of slots defined by a compression member can be defined from the second end toward the first end such that no slots are positioned in the second passageway defined by the bottom member when the compression member is in the first position.

When assembled, the second end 964 of the compression member 916 is disposed within the first passageway 936 defined by the top member 926. In use, rotation of the rotatable member 914 about its lengthwise axis in a first direction moves the threads 956 within the plurality of slots 967 such that the compression member 916 is moved from its first position to its second position. Rotation of the rotatable member 914 about its lengthwise axis in a second direction moves the threads 956 within the plurality of slots 967 such that the compression member 916 is moved from its second position to its first position. Optionally, the magnetically actuated gating device 910 can include a membrane disposed between the compression member 916 and the lengthwise axis 947 of the second passageway 946. For example, a portion of a non-compliant balloon can be attached to the bottom member 928 such that it is disposed over the compression member 916 and contacts a vessel when a vessel is disposed within the second passageway 946.

Methods of treatment are described herein. While the methods described herein are shown and described as a series of acts, it is to be understood and appreciated that the methods are not limited by the order of acts described and illustrated, as some acts may in accordance with these methods, be omitted, be repeated, or occur in different orders and/or concurrently with other acts described herein. The methods include methods of treatment using a magnetically actuated gating device. While some steps, optional steps, and/or alternative steps are exemplified by performing treatment on a vessel, the methods, steps, optional steps, and/or alternative steps described herein can be used to treat any other suitable structure. Skilled artisans will be able to select a suitable structure on which to perform the methods, steps, optional steps, and/or alternative steps described herein based on various considerations, such as the treatment intended to be performed.

Figure 17:
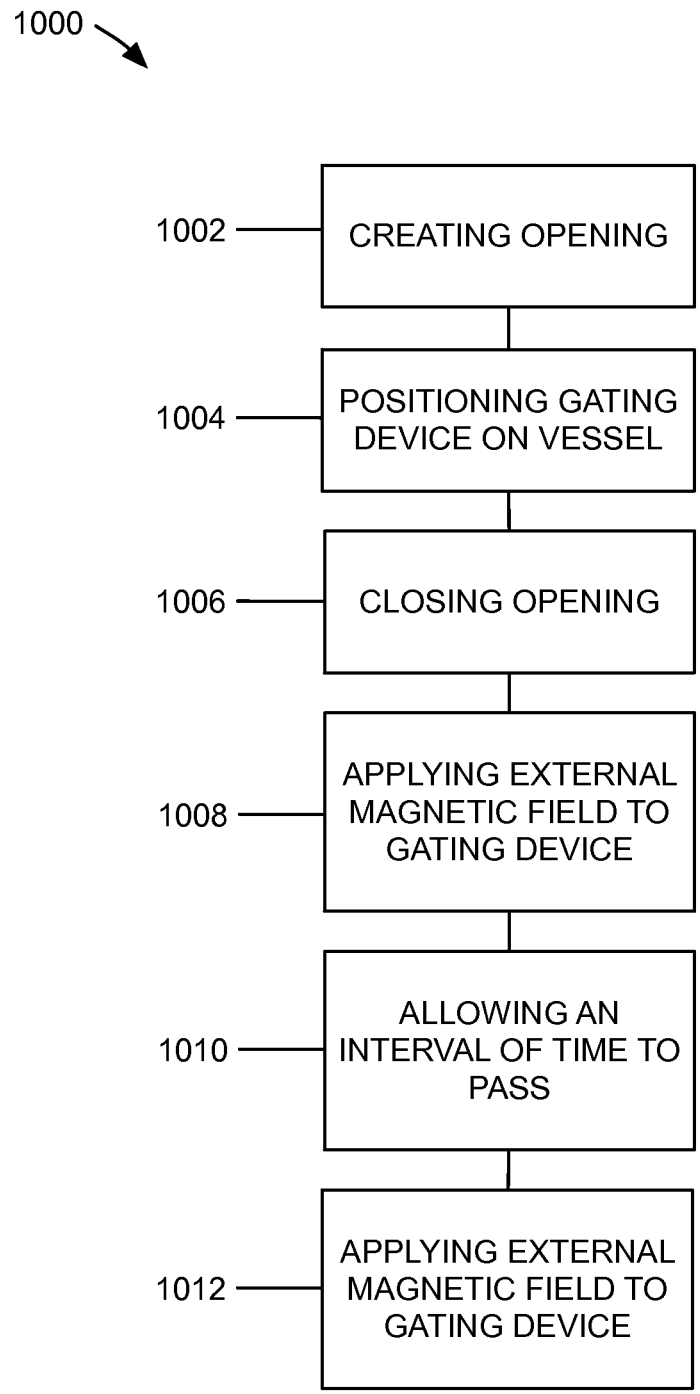
FIG. 17 is a schematic illustration of an example method of treatment.

FIG. 17 is a schematic illustration of an example method of treatment 1000 using a magnetically actuated gating device.

A step 1002 comprises creating an opening in a portion of a body that provides access to a point of treatment. The point of treatment comprises a vessel. Another step 1004 comprises positioning a magnetically actuated gating device on the vessel. Another step 1006 comprises closing the opening that provides access to the point of treatment. Another step 1008 comprises applying an external second magnetic field to the first magnetic field of the magnetically actuated gating device such that the rotatable member moves from the first position to the second position. Another step 1010 comprises allowing an interval of time to pass. Another step 1012 comprises applying an external second magnetic field to the first magnetic field of the magnetically actuated gating device such that the rotatable member moves from the second position to the first position.

Step 1002 can be accomplished using any suitable medical device, such as a scalpel, or any other tool and can be performed using any suitable method and/or technique at any suitable location on a body. For example, in embodiments in which the vessel being treated is an arteriovenous fistula, step 1002 can be accomplished using a scalpel to perform a conventional surgical procedure (e.g., cutdown) to create an opening in the forearm of a patient.

Step 1004 can be accomplished using any suitable magnetically actuated gating device according to an embodiment, such as magnetically actuated gating device 10, magnetically actuated gating device 110, magnetically actuated gating device 210, magnetically actuated gating device 310, magnetically actuated gating device 510, magnetically actuated gating device 610, magnetically actuated gating device 710, magnetically actuated gating device 910, variations thereof, and any other gating device considered suitable for a particular method of treatment. An example magnetically actuated gating device that can be used to accomplish the methods, steps, alternative steps, and/or optional steps described herein is illustrated and described with respect to FIGS. 6, 7A, 7B, 8A, and 8B and comprises a housing 112, a rotatable member 114, a compression member 116, a membrane 118, and a magnetically actuated member 180. The gating device 110 is moveable between a first configuration and a second configuration.

Step 1004 can be accomplished by positioning the vessel within the recess 144 defined by the bottom member 128 and attaching the top member 126 to the bottom member 128 such that the vessel is disposed within the second passageway 146, as illustrated in FIG. 8A. A magnetically actuated gating device can be positioned on any suitable vessel, such as an arteriovenous fistula.

Step 1006 can be accomplished by suturing the opening created to provide access to the point of treatment. This can be accomplished using any suitable medical device and/or structure, such as sutures.

Step 1008 can be accomplished by applying an external second magnetic field to the first magnetic field 158 of the magnetically actuated gating device 110 such that the rotatable member 114 moves from the first position to the second position. Movement of the rotatable member 114 from the first position to the second position moves the membrane 118 from the first position to the second position such that the vessel is compressed and the lumen defined by the vessel has a reduced diameter, as illustrated in FIG. 8B.

An optional step comprises confirming that the rotatable member and/or membrane are in the second position. This optional step can be accomplished using any suitable visualization technique.

Step 1010 can be accomplished by allowing an interval of time to pass. Any suitable interval of time can pass and be based on the treatment being performed. Examples of suitable intervals of time considered suitable include one or more seconds, minutes, hours, days, months, years, and any other interval of time considered suitable for a particular treatment.

Step 1012 can be accomplished by applying an external second magnetic field to the first magnetic field 158 of the magnetically actuated gating device 110 such that the rotatable member 114 moves from the second position to the first position. Movement of the rotatable member 114 from the second position to the first position moves the membrane 118 from the second position to the first position such that the vessel is returned to its original configuration, or a configuration substantially similar to its original configuration, and the diameter of the lumen defined by the vessel returns to its original diameter, or a diameter substantially similar to its original diameter. Step 1012 can optionally be completed prior to, during, or subsequent to treatment being performed, such as dialysis to increase the flow rate through the vessel disposed within the magnetically actuated gating device.

An optional step comprises repeating step 1008 subsequent to a treatment (e.g., dialysis) being performed.

Alternative to completing step 1012, a step that can be completed comprises applying an external second magnetic field to the first magnetic field of the magnetically actuated gating device such that the rotatable member moves from the second position to a position between the second position and the first position. This step can optionally be repeated to gradually increase the diameter of the lumen defined by the vessel over an interval of time to facilitate maturation of the vessel to promote tissue remodeling.

An optional step comprises confirming that the rotatable member and/or membrane are in the first position. This optional step can be accomplished using any suitable visualization technique.

Optionally, any of the steps described herein can be repeated, such as step 1002, step 1004, step 1006, step 1008, step 1010, and/or step 1012.

When it is desired to perform a magnetic resonance imaging scan the following optional steps can be completed. An optional step comprises repeating step 1002. Another optional step comprises removing the rotatable member and/or magnetically actuated member from the magnetically actuated gating device. This step can be accomplished in a variety of different ways and depends on the structural arrangement of the magnetically actuated gating device. For example, this optional step can be accomplished by removing the magnetically actuated gating device or removing the cap of an embodiment and then withdrawing the rotatable member from the first passageway. Alternatively, this step can be accomplished by detaching the top member from the bottom member and withdrawing the rotatable member from the first passageway. Alternatively, this step can be accomplished by detaching the magnetically actuated member from the housing. Another optional step comprises repeating step 1006. Another optional step comprises performing the magnetic resonance imaging scan. Another optional step comprises repeating step 1002. Another optional step comprises inserting the rotatable member and/or magnetically actuated member into the magnetically actuated gating device. This step can be accomplished in a variety of different ways and depends on the structural arrangement of the magnetically actuated gating device. For example, this optional step can be accomplished by positioning the magnetically actuated gating device on the vessel (e.g., step 1004) or removing the cap of an embodiment and then inserting the rotatable member into the first passageway. Alternatively, this step can be accomplished by detaching the top member from the bottom member and inserting the rotatable member into the first passageway. Alternatively, this step can be accomplished by attaching the magnetically actuated member to the housing. Another optional step comprises repeating step 1006.

An optional step comprises removing the magnetically actuated gating device from the vessel. This optional step can be completed by repeating step 1002 and by detaching the bottom member from the top member. Subsequently, another optional step comprises removing the bottom member and the top member from the vessel. Another optional step comprises repeating step 1006.

While the magnetically actuated gating devices described herein have been described as being used on an arteriovenous fistula, the magnetically actuated gating devices described herein can be used on any suitable vessel. Skilled artisans will be able to select a suitable vessel to position a magnetically actuated gating device according to a particular embodiment based on various considerations, including the treatment intended to be performed. For example, the magnetically actuated gating devices described herein can be used on any tubular member, any structure that transports material, any structure that transports material in the body of an animal, walls that define bodily passages, arteries, veins, fistulas, arteriovenous fistulas, capillaries, portions of the urinary tract, lymphatic vessels, vessels in the digestive tract, natural body vessels, prosthetic body vessels, grafts, such as autologous grafts, homologous grafts, or synthetic grafts, and any other structure considered suitable for a particular embodiment.

Figure 18:
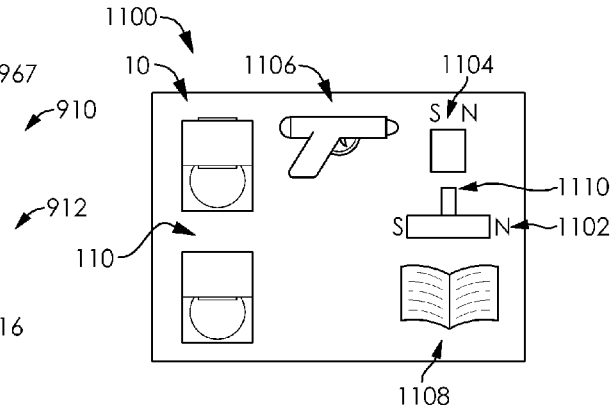
FIG. 18 is a top view of an example embodiment of a kit that includes a magnetically actuated gating device.

FIG. 18 illustrates an example embodiment of a kit 1100 useful in performing a method of treatment, such as those described herein. The kit 1100 includes the magnetically actuated gating device 10 illustrated in FIGS. 1, 2, 3A, and 3B, the magnetically actuated gating device 110 illustrated in FIGS. 6, 7A, 7B, 8A, and 8B, a first element 1102 that has a magnetic field, a second element 1104 that has a magnetic field, a device 1106 for producing rotation in the first element 1102 and/or second element 1104, and instructions for use 1108. Each of the magnetically actuated gating devices 10, 110 is sized and configured to receive a portion of a vessel. First element 1102 comprises a bar magnet that has an attachment member 1110 sized and configured to be received by the device 1106. Second element 1104 comprises a diametrically magnetized cylindrically shaped permanent magnet that is sized and configured to be received by the device 1106. Both of the elements 1102, 1104 are configured to interact with each of the magnetically actuated gating devices 10, 110 to move the magnetically actuated gating device between a first configuration and a second configuration. The device 1106 comprises a surgical drill and is sized and configured to receive a portion the first element 1102 and the second element 1104.

While kit 1100 has been illustrated as including a magnetically actuated gating device 10, a magnetically actuated gating device 110, a first element 1102, and a second element 1104, a kit can include any suitable type and number of magnetically actuated gating devices and elements. Selection of a suitable type and number of magnetically actuated gating devices and elements to include in a kit according to an embodiment can be based on various considerations, such as the procedure intended to be performed and whether sizing of a vessel is desired to determine the appropriate magnetically actuated gating device to position on the vessel. Example magnetically actuated gating devices considered suitable to include in a kit include magnetically actuated gating device 10, magnetically actuated gating device 110, magnetically actuated gating device 210, magnetically actuated gating device 310, magnetically actuated gating device 510, magnetically actuated gating device 610, magnetically actuated gating device 710, magnetically actuated gating device 910, variations thereof, and/or any other gating device considered suitable for a particular embodiment. Example elements that have a magnetic field considered suitable to include in a kit include any suitable element, device, and/or system, that has a magnetic field, or is capable of producing or creating a magnetic field, such as a magnet, a permanent magnet, a bar magnet, an electromagnet, a diametrically magnetized element, a diametrically magnetized cylindrically shaped permanent magnet that is magnetized along an axis of the magnet (e.g., lengthwise axis, an axis that extends through the center of the magnets length or width), an axially magnetized element, an electromagnet that can be rotated, or activated, and/or any other element, device, and/or system considered suitable for a particular embodiment. Alternative embodiments of a kit can omit the inclusion of an element and/or instructions for use. Example numbers of magnetically actuated gating devices and/or elements considered suitable to include in a kit include, one, at least one, two, a plurality, three, four, five, six, seven, eight, nine, ten, and any other number considered suitable for a particular embodiment.

While device 1106 has been illustrated as a surgical drill, any suitable device or component capable of producing rotation in an element that has, or can produce, a magnetic field, such as those described herein, can be used. For example, alternative embodiments of a kit can omit the inclusion of a device and rotation of an element can be produced by hand.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A magnetically actuated gating device for implantation outside of a vessel and adapted to interact with an element located exterior to the vessel, the element having a first magnetic field and moveable in a first direction and a second direction that is substantially opposite the first direction, the magnetically actuated gating device comprising:

a housing defining a first passageway, a second passageway, and a first opening, the first passageway having a first lengthwise axis, the second passageway configured to receive a portion of said vessel and having a second lengthwise axis disposed at an angle to the first lengthwise axis, the first opening providing access between the first passageway and the second passageway;

a rotatable member rotatably attached to the housing and moveable axially along the first lengthwise axis between a first position and a second position, the rotatable member disposed within the first passageway and having a second magnetic field that is adapted to interact with said first magnetic field such that the rotatable member moves from its first position to its second position when said element is moved in said first direction and moves from its second position to its first position when said element is moved in said second direction; and a compression member attached to the rotatable member and adapted to move between a first position in which the compression member is disposed a first distance from the second lengthwise axis and a second position in which the compression member is disposed a second distance from the second lengthwise axis that is different than the first distance, the compression member is in the first position when the rotatable member is in the first position and is in the second position when the rotatable member is in the second position.

2. The magnetically actuated gating device of claim 1, wherein the rotatable member defines a recess;

further comprising a magnetically actuated member attached within the recess defined by the rotatable member, the magnetically actuated member comprising the second magnetic field.

3. The magnetically actuated gating device of claim 1, wherein the first lengthwise axis is disposed orthogonal to the second lengthwise axis.

4. The magnetically actuated gating device of claim 1, further comprising a membrane attached to the housing and disposed over the first opening, the membrane preventing fluid within the second passageway from passing into the first passageway, the membrane adapted to move between a first position in which the membrane is disposed a first distance from the second lengthwise axis and a second position in which the membrane is disposed a second distance from the second lengthwise axis that is different than the first distance, the membrane is in the first position when the rotatable member is in the first position and is in the second position when the rotatable member is in the second position.

5. The magnetically actuated gating device of claim 4, wherein the membrane is attached to the housing between the compression member and the second passageway.

6. The magnetically actuated gating device of claim 4, wherein the membrane is formed of a first material and the housing is formed of a second material that is different than the first material.

7. The magnetically actuated gating device of claim 4, wherein the compression member has a first end rotatably attached to the rotatable member and a second end fixedly attached to the membrane.

8. The magnetically actuated gating device of claim 1, wherein the housing is formed of a top member and a bottom member that is releasably attached to the top member.

9. The magnetically actuated gating device of claim 8, wherein the top member defines the first passageway; and wherein the bottom member cooperatively defines the second passageway with the top member.

10. The magnetically actuated gating device of claim 8, wherein the top member defines threads within the first passageway; and wherein the rotatable member defines threads that are sized and configured to interact with the threads defined by the top member.

11. A magnetically actuated gating device for implantation outside of a vessel and adapted to interact with an element located exterior to the vessel, the element having a first magnetic field and moveable in a first direction and a second direction that is substantially opposite the first direction, the magnetically actuated gating device comprising:

a housing defining a first passageway, a second passageway, and a first opening, the first passageway having a first lengthwise axis, the second passageway configured to receive a portion of said vessel and having a second lengthwise axis disposed at an angle to the first lengthwise axis, the first opening providing access between the first passageway and the second passageway;

a rotatable member rotatably attached to the housing and moveable axially along the first lengthwise axis between a first position and a second position, the rotatable member disposed within the first passageway, having a magnetically actuated member, and defining a recess, the magnetically actuated member attached within the recess and having a second magnetic field that is adapted to interact with said first magnetic field such that the rotatable member moves from its first position to its second position when said element is moved in said first direction and moves from its second position to its first position when said element is moved in said second direction;

a compression member attached to the rotatable member and adapted to move between a first position in which the compression member is disposed a first distance from the second lengthwise axis and a second position in which the compression member is disposed a second distance from the second lengthwise axis that is different than the first distance, the compression member is in the first position when the rotatable member is in the first position and is in the second position when the rotatable member is in the second position; and a membrane attached to the housing and disposed over the first opening, the membrane preventing fluid within the second passageway from passing into the first passageway, the membrane adapted to move between a first position in which the membrane is disposed a first distance from the second lengthwise axis and a second position in which the membrane is disposed a second distance from the second lengthwise axis that is different than the first distance, the membrane is in the first position when the rotatable member is in the first position and is in the second position when the rotatable member is in the second position.

12. The magnetically actuated gating device of claim 11, wherein the first lengthwise axis is disposed orthogonal to the second lengthwise axis.

13. The magnetically actuated gating device of claim 11, wherein the membrane is attached to the housing between the compression member and the second passageway.

14. The magnetically actuated gating device of claim 11, wherein the membrane is formed of a first material and the housing is formed of a second material that is different than the first material.

15. The magnetically actuated gating device of claim 11, wherein the compression member has a first end rotatably attached to the rotatable member and a second end fixedly attached to the membrane.

16. The magnetically actuated gating device of claim 11, wherein the housing is formed of a top member and a bottom member that is releasably attached to the top member.

17. The magnetically actuated gating device of claim 16, wherein the top member defines the first passageway; and wherein the bottom member cooperatively defines the second passageway with the top member.

18. The magnetically actuated gating device of claim 16, wherein the top member defines threads within the first passageway; and wherein the rotatable member defines threads that are sized and configured to interact with the threads defined by the top member.

19. A magnetically actuated gating device for implantation outside of a vessel and adapted to interact with an element located exterior to the vessel, the element having a first magnetic field and moveable in a first direction and a second direction that is substantially opposite the first direction, the magnetically actuated gating device comprising:

a housing defining a first passageway, a second passageway, and a first opening, the housing formed of a first material, the first passageway having a first lengthwise axis, the second passageway configured to receive a portion of said vessel and having a second lengthwise axis that is disposed orthogonal to the first lengthwise axis, the first opening providing access between the first passageway and the second passageway;

a rotatable member rotatably attached to the housing and moveable axially along the first lengthwise axis between a first position and a second position, the rotatable member disposed within the first passageway, having a magnetically actuated member, and defining a recess, the magnetically actuated member attached within the recess and having a second magnetic field that is adapted to interact with said first magnetic field such that the rotatable member moves from its first position to its second position when said element is moved in said first direction and moves from its second position to its first position when said element is moved in said second direction;

a compression member attached to the rotatable member and adapted to move between a first position in which the compression member is disposed a first distance from the second lengthwise axis and a second position in which the compression member is disposed a second distance from the second lengthwise axis that is different than the first distance, the compression member is in the first position when the rotatable member is in the first position and is in the second position when the rotatable member is in the second position; and a membrane attached to the housing and disposed over the first opening between the compression member and the second passageway, the membrane preventing fluid within the second passageway from passing into the first passageway, the membrane adapted to move between a first position in which the membrane is disposed a first distance from the second lengthwise axis and a second position in which the membrane is disposed a second distance from the second lengthwise axis that is different than the first distance, the membrane is in the first position when the rotatable member is in the first position and is in the second position when the rotatable member is in the second position, the membrane formed of a second material that is different than the first material.

20. The magnetically actuated gating device of claim 19, wherein the compression member has a first end rotatably attached to the rotatable member and a second end fixedly attached to the membrane.

* * * * *